(12) United States Patent
Hayasaka et al.

(10) Patent No.: US 9,868,912 B2
(45) Date of Patent: Jan. 16, 2018

(54) METHOD FOR PRODUCING LUBRICANT OIL BASE OIL

(71) Applicant: JX NIPPON OIL & ENERGY CORPORATION, Tokyo (JP)

(72) Inventors: Kazuaki Hayasaka, Tokyo (JP); Yasushi Wada, Tokyo (JP); Marie Iwama, Tokyo (JP); Koshi Takahama, Tokyo (JP)

(73) Assignee: JX NIPPON OIL & ENERGY CORPORATION, Tokyo (JP)

( * ) Notice: Subject to any disclaimer, the term of this patent is extended or adjusted under 35 U.S.C. 154(b) by 39 days.

(21) Appl. No.: 14/780,768

(22) PCT Filed: Mar. 26, 2014

(86) PCT No.: PCT/JP2014/058598
§ 371 (c)(1),
(2) Date: Sep. 28, 2015

(87) PCT Pub. No.: WO2014/157368
PCT Pub. Date: Oct. 2, 2014

(65) Prior Publication Data
US 2016/0053187 A1    Feb. 25, 2016

(30) Foreign Application Priority Data

Mar. 29, 2013    (JP) .................................. 2013-074792

(51) Int. Cl.
*C10G 45/64* (2006.01)
*C10G 45/58* (2006.01)
(Continued)

(52) U.S. Cl.
CPC ............. *C10G 45/64* (2013.01); *C10G 45/58* (2013.01); *C10M 101/02* (2013.01);
(Continued)

(58) Field of Classification Search
CPC .... C10G 45/58; C10G 45/64; C10G 2400/10; G01N 24/08; G01N 24/085; G01N 24/087;
(Continued)

(56) References Cited

U.S. PATENT DOCUMENTS

| 6,773,578 B1 | 8/2004 | O'Rear et al. |
| 2005/0077208 A1* | 4/2005 | Miller .................. C10M 107/02 208/18 |

(Continued)

FOREIGN PATENT DOCUMENTS

| CN | 101235330 A | 8/2008 |
| CN | 102239241 A | 11/2011 |

(Continued)

OTHER PUBLICATIONS

International Search Report issued in Patent Application No. PCT/JP2014/058598, dated Jun. 24, 2014.

(Continued)

*Primary Examiner* — Prem C Singh
*Assistant Examiner* — Brandi M Doyle
(74) *Attorney, Agent, or Firm* — Greenblum & Bernstein, P.L.C.

(57) ABSTRACT

A method for producing a lubricating base oil, comprising: performing a $^{13}$C-NMR analysis regarding an oil to be treated and selecting the oil based on a value for dividing an integrated value of a peak for a tertiary carbon atom by an integrated value of all peaks at 0 to 50 ppm, a value for dividing an integrated value of a peak for a carbon atom constituting a main chain by the integrated value of all peaks at 0 to 50 ppm, and a value for dividing an integrated value of a peak for a branched $CH_3$ bonded to a fifth or the following carbon atom from a terminal carbon atom in the main chain by an integrated value of all peaks at 10 to 25

(Continued)

ppm, and obtaining a dewaxed oil by isomerization dewaxing of the oil selected in the first step, is disclosed.

5 Claims, 2 Drawing Sheets

(51) Int. Cl.
*G01N 24/08* (2006.01)
*C10M 101/02* (2006.01)

(52) U.S. Cl.
CPC ............ *G01N 24/08* (2013.01); *G01N 24/085* (2013.01); *C10G 2400/10* (2013.01); *C10M 2203/0206* (2013.01); *C10N 2220/022* (2013.01); *C10N 2230/02* (2013.01)

(58) Field of Classification Search
CPC ........ C10M 101/02; C10M 2203/0206; C10N 2230/02; C10N 2220/022
See application file for complete search history.

(56) References Cited

U.S. PATENT DOCUMENTS

| 2008/0116108 A1 | 5/2008 | Zhang et al. |
| 2011/0237477 A1 | 9/2011 | Tagawa et al. |

FOREIGN PATENT DOCUMENTS

| CN | 102459543 A | 5/2012 |
| CN | 102712869 A | 10/2012 |
| JP | 2004-515601 | 5/2004 |
| JP | 2008-520770 | 6/2008 |
| JP | 2008-274236 | 11/2008 |
| WO | 2010/041689 | 4/2010 |

OTHER PUBLICATIONS

English translation of International Preliminary Report on Patentability issued in PCT/JP2014/058598, dated Oct. 8, 2015.

* cited by examiner

METHOD FOR PRODUCING LUBRICANT OIL BASE OIL

TECHNICAL FIELD

The present invention relates to a method for producing a lubricating base oil.

BACKGROUND ART

Conventionally, in the field of lubricating base oils, attempts to improve cold flow property and a low-temperature viscosity property of a base oil contained in a lubricant (lubricating base oil) have been executed.

In a process of producing a lubricating base oil, treatment of reducing the content ratio of a normal paraffin contained in a lubricating base oil (dewaxing treatment) is generally performed so as to improve cold flow property. Thus, in a producing step of a lubricating base oil, dewaxing treatment such as solvent dewaxing and isomerization dewaxing is widely performed.

Solvent dewaxing is a treatment in which an oil to be treated (lubricating base oil before dewaxing treatment) is mixed with a solvent to be cooled and a deposit (wax component) in the mixture is removed by filtration or the like. Moreover, isomerization dewaxing is a treatment in which a wax component in an oil to be treated is reduced by, in the presence of hydrogen, bringing the oil to be treated into contact with an isomerization dewaxing catalyst to convert (isomerize) mainly a normal paraffin into an isoparaffin. Although isomerization of a normal paraffin to an isoparaffin may occur in hydrocracking that is one of hydrotreatment, while cracking of various components contained in an oil to be treated is main in hydrocracking, isomerization is main in isomerization dewaxing, and thus, both are distinguished.

Furthermore, Patent Literature 1 discloses a method for producing a lubricating base oil, in which the contents of a normal paraffin that has a harmful effect on cold flow property and a specific isoparaffin are reduced by performing hydrocracking/isomerization dewaxing such that the urea adduct value of an obtained lubricating base oil is within a predetermined range.

CITATION LIST

Patent Literature

Patent Literature 1: JP-A-2008-274236

SUMMARY OF INVENTION

Technical Problem

Regarding performance of a lubricating base oil, from the viewpoint of energy saving, a low-temperature viscosity property is important as well as cold flow property, and attempts for improvement have been executed. In general, a low-temperature viscosity property of a base oil is expressed by a value of a viscosity index, and a larger viscosity index causes a smaller viscosity change due to temperature and indicates being an excellent lubricating base oil. In the case of performing isomerization dewaxing in a method for producing a lubricating base oil, a normal paraffin needs to be completely converted into an isoparaffin. On the other hand, there was a problem in that, when the conversion reaction progresses too much, a viscosity index of a lubricating base oil is decreased in a region where the isomer ratio (ratio of isoparaffin component/paraffin component in obtained lubricating base oil) is 100% or approximately 100%.

According to the present inventors' knowledge, increasing of a degree of branching (branching degree) per one molecule of an isoparaffin is one of the causes of a phenomenon in which a viscosity index of a lubricating base oil is decreased when the isomer ratio is increased. It is not always easy to adjust the branching degree by selecting a treatment condition of isomerization dewaxing. In addition, if desirable lubricating base oil can be obtained, a yield may be insufficient in that case.

The present invention has been made in view of these circumstances, and it is an object of the present invention to provide a method for producing a lubricating base oil capable of obtaining a lubricating base oil having a high viscosity index and superior flow property at a high yield.

Solution to Problem

The present inventors made extensive research so as to achieve the above-described object, and found that, in order to achieve both a high viscosity index and superior cold flow property in an obtained lubricating base oil, selection of an oil to be treated which is subjected to isomerization dewaxing is important and as an index when selecting such an oil to be treated, a specific parameter derived from a $^{13}$C-NMR spectrum is useful to complete the present invention.

More specifically, the present invention provides a method for producing a lubricating base oil comprising:

a first step of performing a $^{13}$C-NMR analysis with respect to an oil to be treated containing a normal paraffin and an isoparaffin, and selecting the oil to be treated based on the following index values (1), (2) and (3) in an obtained $^{13}$C-NMR spectrum, index value (1): a value obtained by dividing an integrated value of a peak assigned to a tertiary carbon atom by an integrated value of all peaks at 0 to 50 ppm, index value (2): a value obtained by dividing an integrated value of a peak assigned to a carbon atom constituting a hydrocarbon main chain by the integrated value of all peaks at 0 to 50 ppm, and index value (3): a value obtained by dividing an integrated value of a peak assigned to a branched $CH_3$ bonded to a fifth carbon atom or a carbon atom on an inner side thereof from a terminal carbon atom in the hydrocarbon main chain by an integrated value of all peaks at 10 to 25 ppm, and a second step of obtaining a dewaxed oil by isomerization dewaxing of the oil to be treated selected in the first step.

Here, the concept of the above-described index values (1), (2) and (3) will be explained with reference to FIG. 1 and the following formula (1). FIG. 1 is an explanatory diagram showing one example of a $^{13}$C-NMR spectrum measured with respect to an oil to be treated containing a normal paraffin and an isoparaffin. In addition, the following formula (1) shows one example of the isoparaffin contained in the oil to be treated.

[Chemical Formula 1]

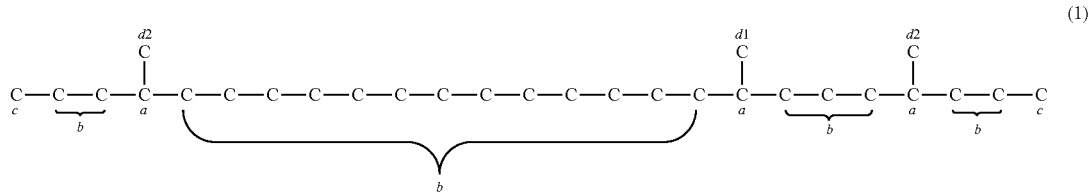

(1)

The $^{13}$C-NMR spectrum in FIG. 1 was obtained by putting a sample in which the oil to be treated is dissolved in deuterated chloroform (the concentration of the oil to be treated is 15 to 25% by volume) in a φ10 mm sample tube and performing measurement, using AVANCE400 (9.4 T) manufactured by Bruker Corporation as an instrument. Firstly, the measurement was performed by a $^{1}$H-gated decoupling method at a 30° pulse, wait time of 10 seconds, and a temperature of 60° C. to detect a chemical shift. In addition, the $^{1}$H resonance frequency was 400 MHz. The measurement was continuously performed by a DEPT135 method under the same conditions, and assignment of peaks of primary/tertiary carbon atoms and secondary carbon atoms was performed. In each measurement, the cumulative number of the spectrum was 2560 times.

In FIG. 1, peaks existing in the region A (25 to 42 ppm), except peaks existing at 29.9±0.2 ppm in FIG. 1, which are assigned to secondary carbon atoms b in the formula (1)) are peaks assigned to tertiary carbon atoms (carbon atoms a in the formula (1)). Moreover, the peaks at 29.9±0.2 ppm in FIG. 1 are peaks assigned to the secondary carbon atoms constituting a hydrocarbon main chain (the carbon atoms b in the formula (1)). Furthermore, peaks existing in the region C (10 to 16 ppm), peaks at 19.9±0.2 ppm, and peaks existing in the region D (16 to 25 ppm, except the peaks existing at 19.9±0.2 ppm in FIG. 1, which are assigned to a carbon atom d1 in the formula (1)) are assigned to terminal $CH_3$ of the hydrocarbon main chain (carbon atoms c in the formula (1)), branched $CH_3$ bonded to a fifth carbon atom or a carbon atom on the inner side thereof from the terminal carbon atom in the hydrocarbon main chain (the carbon atom d1 in the formula (1)), and branched $CH_3$ bonded to second to fourth carbon atoms from the terminal carbon atom in the hydrocarbon main chain (carbon atoms d2 in the formula (1)), respectively.

As can be seen from the comparison between the $^{13}$C-NMR spectrum shown in FIG. 1 and the isoparaffin represented by the formula (1), when the branching degree of the hydrocarbon contained in the oil to be treated is large, the index value (1) becomes large. In addition, when the branching degree is large, the ratio of constituent carbon atoms of the hydrocarbon main chain to all carbon atoms becomes relatively small, and the index value (2) becomes small. In contrast, in the case where the hydrocarbon main chain is long, the branched chain is short, the branching degree is small or the like, the ratio of constituent carbon atoms of the hydrocarbon main chain to all carbon atoms becomes large, and the index value (2) becomes large. Moreover, when the branched $CH_3$ bonded to the fifth carbon atom or the carbon atom on the inner side thereof from the terminal carbon atom in the hydrocarbon main chain is large in number, the index value (3) becomes large.

According to the present invention, by selecting the oil to be treated based on the above-described index values (1), (2) and (3), and subjecting the selected oil to be treated to isomerization dewaxing, from the viewpoints of a viscosity index and cold flow property, a dewaxed oil having an appropriately branching degree can be easily and efficiently obtained. Therefore, it becomes possible to obtain a lubricating base oil having a high viscosity index and superior cold flow property at a high yield.

Although, in the first step, the criterion of selecting based on the index values (1), (2) and (3) can be appropriately determined in accordance with a treatment condition of isomerization dewaxing, characteristics of an intended lubricating base oil (dewaxed oil) and the like, in the case where, for example, the second step is a step of performing isomerization dewaxing of the oil to be treated selected in the first step at a reaction temperature of 280 to 360° C., the first step is preferably a step of selecting the oil to be treated having the index value (1) of 0.01 to 0.1, the index value (2) of 0.2 to 0.6, and the index value (3) of 0.05 to 0.2. By subjecting the oil to be treated satisfying these conditions to isomerization dewaxing, a lubricating base oil that achieves both a high viscosity index (for example, viscosity index of 140 or more) and superior cold flow property (for example, pour point of −25° C. or less) can be produced at a high yield (for example, base oil yield of 60% or more on the basis of dewaxing raw material).

Advantageous Effects of Invention

According to the present invention, a method for producing a lubricating base oil capable of obtaining a lubricating base oil that achieves both a high viscosity index and superior cold flow property at a high yield is provided.

DESCRIPTION OF EMBODIMENTS

Figure 1:
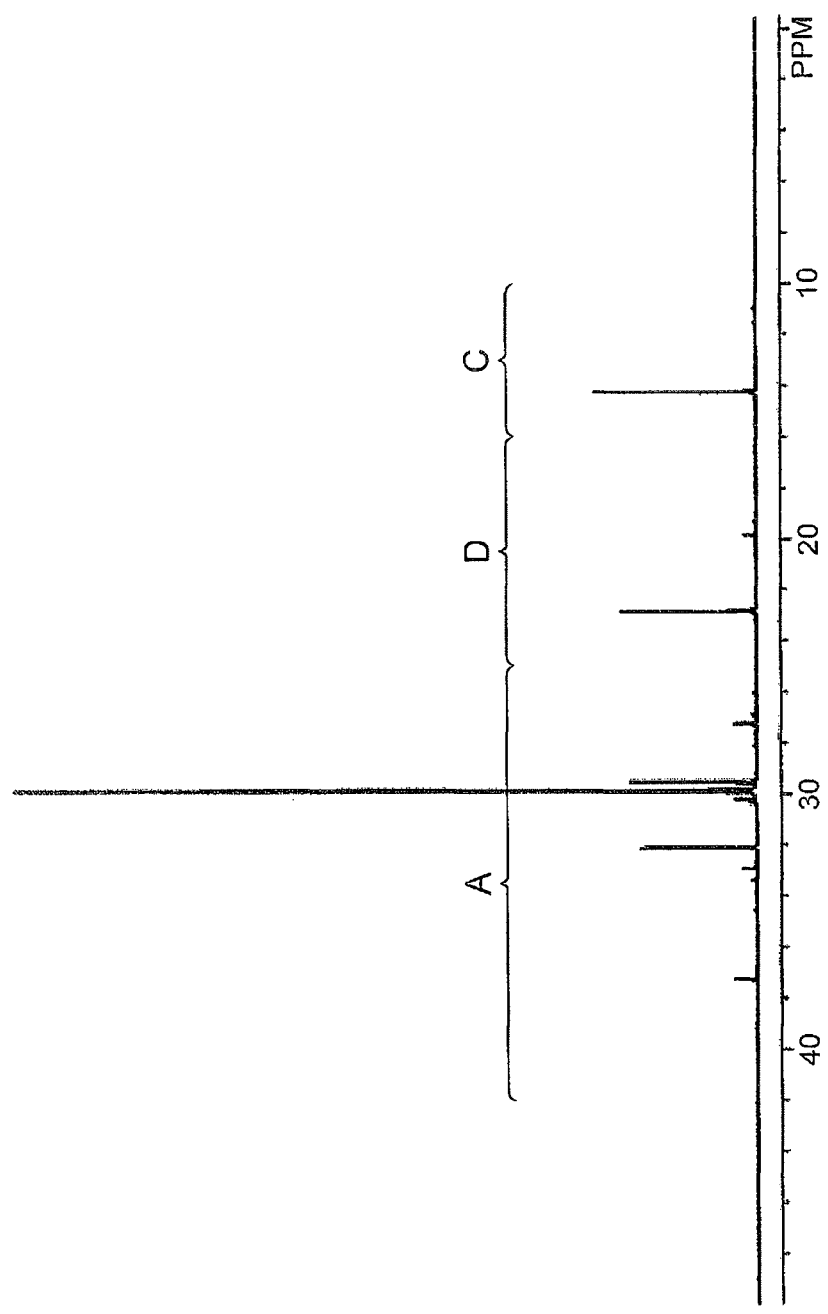
FIG. 1 is an explanatory diagram showing one example of a $^{13}$C-NMR spectrum measured with respect to an oil to be treated containing a normal paraffin and an isoparaffin.

Preferred embodiments of the present invention will now be described.

A method for producing a lubricating base oil according to the present embodiment includes a first step of performing a $^{13}$C-NMR analysis with respect to an oil to be treated containing a normal paraffin and an isoparaffin, and selecting the oil to be treated based on the following index values (1), (2) and (3) in an obtained $^{13}$C-NMR spectrum, index value (1): a value obtained by dividing an integrated value of a peak assigned to a tertiary carbon atom by an integrated value of all peaks at 0 to 50 ppm, index value (2): a value obtained by dividing an integrated value of a peak assigned to a carbon atom constituting a hydrocarbon main chain by the integrated value of all peaks at 0 to 50 ppm, and index value (3): a value obtained by dividing an integrated value of a peak assigned to a branched $CH_3$ bonded to a fifth carbon atom or a carbon atom on the inner side thereof from a terminal carbon atom in the hydrocarbon main chain by an integrated value of all peaks at 10 to 25 ppm, and a second step of obtaining a dewaxed oil by isomerization dewaxing of the oil to be treated selected in the first step.

In addition, when satisfying the criterion of selecting based on the index values (1), (2) and (3), the oil to be treated to be subjected to the first step can be appropriately selected from atmospheric residue, hydrocracked atmospheric residue, vacuum residue, hydrocracked vacuum residue, hydrotreated gas oil, heavy gas oil, vacuum gas oil, hydrocracked vacuum gas oil, lubricant raffinate, lubricant raw material, bright stock, slack wax (crude wax), foot's oil, deoiled wax, paraffin wax, microcrystalline wax, petrolatum, synthetic oils, Fischer-Tropsch synthesis reaction oil, high-pour-point polyolefins, straight-chain α-olefin waxes and the like, without performing a pre-treatment step described below.

Moreover, the method for producing a lubricating base oil according to the present embodiment may include a step of obtaining a pre-treated hydrocarbon oil by performing pre-treatment of a hydrocarbon oil (hereinafter, referred to as "pre-treatment step" in some cases) and a step of obtaining the oil to be treated by fractionating the pre-treated hydrocarbon oil (hereinafter, referred to as "raw material distillation step" in some cases) before the above-described first step. The pre-treated hydrocarbon oil obtained through such a pre-treatment step can be used as the oil to be treated.

(Pre-Treatment Step)

In the pre-treatment step, the pre-treatment of the hydrocarbon oil is performed to obtain the pre-treated hydrocarbon oil. Examples of the pre-treatment include hydrocracking treatment and hydroisomerization treatment.

Examples of the hydrocarbon oil as a raw material in the pre-treatment step include atmospheric residue, hydrocracked atmospheric residue, vacuum residue, hydrocracked vacuum residue, hydrotreated gas oil, heavy gas oil, vacuum gas oil, hydrocracked vacuum gas oil, lubricant raffinate, lubricant raw material, bright stock, slack wax (crude wax), foot's oil, deoiled wax, paraffinic wax, microcrystalline wax, petrolatum, synthetic oils, Fischer-Tropsch synthesis reaction oil, high-pour-point polyolefins, and straight-chain α-olefin waxes. These hydrocarbon oils can be used singly or in combinations of two or more. Especially preferred as the hydrocarbon oil is at least one selected from the group consisting of vacuum gas oil, hydrocracked vacuum gas oil, atmospheric residue, hydrocracked atmospheric residue, vacuum residue, hydrocracked vacuum residue, slack wax, dewaxed oil, paraffin wax, microcrystalline wax, petrolatum, and FT synthetic oil. In the present specification, a synthetic oil synthesized by a Fischer-Tropsch reaction is referred to as "FT synthetic oil." A wax component included in FT synthetic oil is referred to as "FT wax."

The FT synthetic oil can be produced by the following method, for example. First, desulfurization of natural gas which is a raw material of the FT synthetic oil is carried out. Sulfur compounds in the natural gas can be converted into hydrogen sulfide by a hydrodesulfurization catalyst, and removed using a hydrogen sulfide adsorbent material.

A high-temperature synthesis gas having carbon monoxide gas and hydrogen gas as main components is produced by a reformation reaction (reforming) of the desulfurized natural gas. The natural gas reformation reaction is represented by the chemical reaction formulae (1) and (2). The reformation method is not limited to a water vapor/carbon dioxide gas reformation method that uses carbon dioxide and water vapor. For example, a water vapor reformation method, a partial oxidation reformation method (PDX) that uses oxygen, an auto-thermal reformation method (ATR) that is a combination of a partial oxidation reformation method and a water vapor reformation method, and a carbon dioxide gas reformation method can also be utilized.

$$CH_4 + H_2O \rightarrow CO + 3H_2 \tag{1}$$

$$CH_4 + CO_2 \rightarrow 2CO + 2H_2 \tag{2}$$

The hydrogen gas and the carbon monoxide gas in the synthesis gas are reacted. Namely, the FT synthetic oil is produced by making an FT reaction like that illustrated in the chemical reaction formula (3) proceeds.

$$(2n+1)H_2 + nCO \rightarrow C_nH_{2n+2} + nH_2O \tag{3}$$

As a catalyst for the FT reaction (FT catalyst), a catalyst in which an active metal is supported on an inorganic support can be used. Examples of the inorganic support include a porous oxide such as silica, alumina, titania, magnesia, and zirconia. Examples of the active metal include cobalt, ruthenium, iron, and nickel. In addition to the above-described active metals, a compound including a metal element of zirconium, titanium, hafnium, sodium, lithium, magnesium and the like may also be supported on the FT catalyst. These components improve catalytic activity and contribute to the control of the number of carbon atoms and its distribution in the FT synthetic oil.

The FT synthetic oil synthesized by the above method is a mixture of straight-chain hydrocarbons (normal paraffins) having about 1 to 100 carbon atoms, which hardly includes any aromatic hydrocarbons, naphthenic hydrocarbons, or isoparaffin. In the FT synthetic oil, an FT wax is included that has about 17 or more carbon atoms, and a boiling point exceeding about 330° C. It is preferred that the FT wax content in the FT synthetic oil is 30% by mass or more. By appropriately adjusting the above-described reaction conditions, the FT wax content can be easily controlled.

Further, in another aspect of the present invention, it is preferred to use as the hydrocarbon oil a petroleum-derived hydrocarbon oil containing petroleum-derived hydrocarbons. Examples of the petroleum-derived hydrocarbon oil include hydrocracked vacuum gas oil, hydrocracked atmospheric residue, hydrocracked vacuum residue, slack wax (crude wax), foot's oil, deoiled wax, paraffinic wax, and microcrystalline wax.

A vacuum gas oil, which is a distillate oil obtained from a crude oil vacuum distillation apparatus, is a hydrocarbon oil that has a boiling point range of about 350 to 550° C. Further, an atmospheric residue, which is a bottom oil extracted from an atmospheric distillation apparatus, is a hydrocarbon oil that has a boiling point range of 350° C. or more. In addition, a vacuum residue, which is a bottom oil extracted from a vacuum distillation apparatus, is a hydrocarbon oil that has a boiling point range of 550° C. or more. A hydrocracked vacuum gas oil is a hydrocarbon oil obtained by hydrocracking a vacuum gas oil. A hydrocracked atmospheric residue is a hydrocarbon oil obtained by hydrocracking an atmospheric residue. A hydrocracked vacuum residue is a hydrocarbon oil obtained by hydrocracking a vacuum residue. Further, it is desirable that the hydrocracked vacuum gas oil, hydrocracked atmospheric residue, and hydrocracked vacuum residue are each used as products obtained by performing a desulfurization treatment to remove sulfur to the extent that the catalyst in the second step does not excessively deteriorate.

<Hydrocracking Treatment>

The hydrocracking treatment can be carried out by, in the presence of hydrogen, bringing the hydrocarbon oil into contact with a hydrocracking catalyst. As the hydrocarbon oil, a heavy FT synthetic oil, a petroleum-derived hydrocarbon oil or the like can be used. Here, the heavy FT synthetic oil means an FT synthetic oil having a boiling point range of 520 to 600° C. The petroleum-derived hydrocarbon oil may be one having a carbon number of 30 or more and the content ratio of a heavy component of 80% by mass.

When the hydrocarbon oil is heavy FT synthetic oil, for example, it is preferred to use as the hydrocracking catalyst a catalyst (hereinafter, referred to as a "hydrocracking catalyst A-1") in which at least one active metal selected from metals of groups 8 to 10 of the periodic table is supported on an inorganic support that is a solid acid. Especially, when the hydrocarbon oil is heavy FT synthetic oil, it is preferred to use the hydrocracking catalyst A-1, because there is less risk of catalyst poisoning due to sulfur content.

Examples of the inorganic support that is a solid acid in the hydrocracking catalyst A-1 include supports formed from one or more inorganic compounds selected from the group consisting of crystalline zeolites, such as ultrastable Y-type (USY) zeolite, Y-type zeolite, mordenite, and β-zeolite, as well as amorphous composite metal oxides such as silica-alumina, silica-zirconia, and alumina-boria. Among these, preferred are supports formed from a USY-type zeolite and one or more amorphous composite metal oxides, such as silica-alumina, alumina-boria, and silica-zirconia, and more preferred are supports formed from a USY-type zeolite and alumina-boria and/or silica-alumina.

A USY-type zeolite is a zeolite that has been made ultrastable by hydrothermally treating or acid treating a Y-type zeolite. A USY-type zeolite has the fine pore structure that a Y-type zeolite inherently has. This fine pore structure is a structure formed from micropores having a pore size of 2 nm or less. In a USY-type zeolite, in addition to the above-described fine pore structure, new pores having a pore size of 2 to 10 nm are additionally formed. The average particle size of the USY-type zeolite, which although is not especially limited, is preferably 1.0 μm or less, and more preferably 0.5 μm or less. Further, the silica/alumina molar ratio (molar ratio of silica based on alumina) in the USY-type zeolite is preferably 10 to 200, more preferably 15 to 100, and even more preferably 20 to 60.

It is preferred that the support of the hydrocracking catalyst A-1 includes 0.1 to 80% by mass of crystalline zeolite and 0.1 to 60% by mass of amorphous composite metal oxide.

A binder may be blended in the support of the hydrocracking catalyst A-1 in order to improve the extrudability and the mechanical strength of the support. Examples of a preferred binder include alumina, silica, titania, and magnesia. Among these, alumina is preferred. The amount of the binder blended, which although is not especially limited, is preferably 20 to 98% by mass, and more preferably 30 to 96% by mass, based on the total mass of the support.

It is preferred that the support of the hydrocracking catalyst A-1 is extruded. Examples of the shape of the extruded support include, but are not especially limited to, a spherical shape, a cylindrical shape, an irregular cylindrical shape having a three leaf shaped or a four leaf shaped cross-section, and a disk shape. As the method for extruding the support, a known method such as extrusion and compression extruding can be used without limitation. The extruded support is normally calcined.

The support of the hydrocracking catalyst A-1 can be produced by, for example, forming a support composition including the above-described inorganic compound that is a solid acid and the binder, and then calcining.

It is preferred that the blending ratio of the inorganic compound that is a solid acid is, based on the total mass of the support composition, 1 to 70% by mass, and more preferred is 2 to 60% by mass. Further, if the support composition includes a USY-type zeolite, it is preferred that the blending ratio of the USY-type zeolite is, based on the total mass of the support composition, 0.1 to 10% by mass, and more preferred is 0.5 to 5% by mass. Still further, if the support composition includes a USY-type zeolite and alumina-boria, it is preferred that the blending ratio of the USY-type zeolite and the alumina-boria (USY-type zeolite/alumina-boria) is 0.03 to 1 by mass. Moreover, if the support composition includes a USY-type zeolite and silica-alumina, it is preferred that the blending ratio of the USY-type zeolite and the silica-alumina (USY-type zeolite/silica-alumina) is 0.03 to 1 by mass.

It is preferred that the temperature when calcining the support composition is in the range of 400 to 550° C., more preferred is in the range of 470 to 530° C., and even more preferred is in the range of 490 to 530° C. By calcining at such a temperature, sufficient solid acidity and mechanical strength can be imparted to the support.

It is preferred that the active metal that the hydrocracking catalyst A-1 has is at least one selected from the group consisting of metals of group 6, group 8, group 9, and group 10 of the periodic table. Specific examples of these metals include noble metals such as platinum, palladium, rhodium, ruthenium, iridium, and osmium, or cobalt, nickel, molybdenum, tungsten, and iron. Preferred are platinum, palladium, nickel, cobalt, molybdenum, and tungsten, and more preferred are platinum and palladium. In addition, it is also preferred to use these metals in combinations of a plurality of species. In this case, examples of preferred combinations include platinum-palladium, cobalt-molybdenum, nickel-molybdenum, nickel-cobalt-molybdenum, and nickel-tungsten.

These active metals may be supported on the above-described support by a conventional method such as impregnation or ion exchange. Although there is no particular limitation on the amount of supported metal, it is preferred that the total amount of metal is 0.1 to 3.0% by mass based on the support mass.

When the hydrocracking catalyst A-1 is used, the hydrocracking reaction temperature can be set at, for example, 180 to 400° C., is preferably 200 to 370° C., more preferably 250 to 300° C., and especially preferably 280 to 350° C. If the reaction temperature is more than 400° C., not only does the yield of the base oil fraction decrease due to the pre-treated hydrocarbon oil fraction being broken down into a light fraction, but the generated product is colored, so that usage as a fuel oil base tends to be limited. On the other hand, if the reaction temperature is less than 180° C., the hydrocracking reaction does not proceed sufficiently, so that the yield of the pre-treated hydrocarbon oil fraction tends to decrease.

When the hydrocracking catalyst A-1 is used, the hydrocracking hydrogen partial pressure may be set at, for example, 0.5 to 12 MPa, and is preferably 1.0 to 5.0 MPa. If the hydrogen partial pressure is less than 0.5 MPa, the hydrocracking tends not to proceed sufficiently. If the hydrogen partial pressure is more than 12 MPa, a high pressure resistance is required for the apparatus, so that equipment costs tend to increase.

When the hydrocracking catalyst A-1 is used, the liquid hourly space velocity (LHSV) of the heavy FT synthetic oil in the hydrocracking may be set at, for example, 0.1 to 10.0 $h^{-1}$, and is preferably 0.3 to 3.5 $h^{-1}$. If the LHSV is less than 0.1 $h^{-1}$, the hydrocracking tends to proceed excessively, and the productivity tends to decrease. If the LHSV is more than 10.0 $h^{-1}$, the hydrocracking tends not to proceed sufficiently.

When the hydrocracking catalyst A-1 is used, the hydrogen/oil ratio in the hydrocracking may be set at, for example, 50 to 1,000 $Nm^3/m^3$, and is preferably 70 to 800 $Nm^3/m^3$. If the hydrogen/oil ratio is less than 50 $Nm^3/m^3$, the hydrocracking tends not to proceed sufficiently. If the hydrogen/oil ratio is more than 1,000 $Nm^3/m^3$, large-scale hydrogen supply apparatus and the like tend to be required.

When the hydrocarbon oil is a petroleum-based hydrocarbon oil, sulfur content can be contained in the petroleum-derived hydrocarbon oil. In such a case, it is preferred to use, as a hydrocracking catalyst, a catalyst (hereinafter referred to as a "hydrocracking catalyst A-2") having a porous inorganic oxide that includes two or more elements selected from aluminum, silicon, zirconium, boron, titanium, and magnesium, and one or more metals selected from the elements of group 6, group 8, group 9, and group 10 of the periodic table that are supported on the porous inorganic oxide. According to the hydrocracking catalyst A-2, decrease in the catalytic activity due to sulfur poisoning is sufficiently suppressed.

As the support of the hydrocracking catalyst A-2, as described above, a porous inorganic oxide formed from two or more selected from aluminum, silicon, zirconium, boron, titanium, and magnesium can be used. Such a porous inorganic oxide is, from the perspective of enabling a much greater improvement in the hydrocracking activity, preferably an inorganic oxide that includes two or more selected from aluminum, silicon, zirconium, boron, titanium, and magnesium, and more preferably an inorganic oxide (a composite oxide of an aluminum oxide and another oxide) that includes aluminum and another element. The support of the hydrocracking catalyst A-2 can also be the inorganic support that is a solid acid used for the above-described hydrocracking catalyst A-1.

If the porous inorganic oxide contains aluminum as a constituent element, the content of aluminum is preferably 1 to 97% by mass, more preferably 10 to 97% by mass, and even more preferably 20 to 95% by mass in terms of alumina, based on the total amount of the porous inorganic oxide. If the content of aluminum is less than 1% by mass in terms of alumina, physical properties such as the support acid properties are not preferable, and a sufficient hydrocracking activity tends not to be exhibited. On the other hand, if the content of aluminum is more than 97% by mass in terms of alumina, the catalyst surface area is insufficient and the activity tends to decrease.

The method for introducing silicon, zirconium, boron, titanium, and magnesium, which are constituent elements of the support other than aluminum, into the support is not especially limited. A solution containing these elements or the like may be used as a raw material. For example, there may be used, for silicon, silicon, liquid glass, and silica sol; for boron, boric acid; for phosphorus, phosphoric acid and an alkali metal salt of phosphoric acid; for titanium, titanium sulfide, titanium tetrachloride, and various alkoxide salts; and for zirconium, zirconium sulfate and various alkoxide salts.

Further, the porous inorganic oxide preferably contains phosphorus as a constituent element. The content of phosphorus is preferably 0.1 to 10% by mass, more preferably 0.5 to 7% by mass, and even more preferably 2 to 6% by mass based on the total amount of the porous inorganic oxide. If the content of phosphorus is less than 0.1% by mass, sufficient hydrocracking activity tends not to be exhibited, and if the content of phosphorus is more than 10% by mass, excessive cracking can proceed.

It is preferred to add the raw materials for the constituent components of the support other than the above-described aluminum oxide in a step before the calcining of the support. For example, the raw materials are added to an aluminum aqueous solution in advance and then an aluminum hydroxide gel containing these constituent components may be prepared or the raw materials may be added to the prepared aluminum hydroxide gel. Alternatively, the raw materials may be added in a step in which water or an acidic aqueous solution is added to a commercially available aluminum oxide intermediate or a boehmite powder, and the resulting mixture is kneaded. However, it is preferred that the raw materials are allowed to coexist during the stage of preparing the aluminum hydroxide gel. Although the mechanism for exhibiting the effect of the constituent components of the support other than aluminum oxide is not entirely understood, it is thought that the constituent components form a complex oxide state with aluminum, and that this causes an increase in the support surface area and interactions with the active metals to occur, thereby influencing the activity.

One or more metals selected from the elements of group 6, group 8, group 9, and group 10 of the periodic table is supported on the above-described porous inorganic oxide acting as a support. Among these metals, it is preferred to use a combination of two or more metals selected from cobalt, molybdenum, nickel, and tungsten. Examples of preferred combinations include cobalt-molybdenum, nickel-molybdenum, nickel-cobalt-molybdenum, and nickel-tungsten. Among these, more preferred is a combination of nickel-molybdenum, nickel-cobalt-molybdenum, and nickel-tungsten. During the hydrocracking, these metals are converted into a sulfide state to use.

As the content of the active metal based on the catalyst mass, the range of the total amount of tungsten and molybdenum supported is preferably 12 to 35% by mass, and more preferably 15 to 30% by mass, in terms of the oxide. If the total amount of tungsten and molybdenum supported is less than 12% by mass, the active sites decrease and sufficient activity tends not to be obtained. On the other hand, if the total amount of tungsten and molybdenum supported is more than 35% by mass, the metals are not effectively dispersed and sufficient activity tends not to be obtained. The range of the total amount of cobalt and nickel supported is preferably 1.0 to 15% by mass and more preferably 1.5 to 12% by mass in terms of the oxide. If the total amount of cobalt and nickel supported is less than 1.0% by mass, a sufficient co-catalyst effect is not obtained and the activity tends to decrease. On the other hand, if the total amount of cobalt and nickel supported is more than 15% by mass, the metals are not effectively dispersed and sufficient activity tends not to be obtained.

It is preferable that phosphorous be supported on the above-described porous inorganic oxide as a support together with the active metal, as an active component. The amount of phosphorous supported on the support is preferably 0.5 to 10% by mass, and more preferably 1.0 to 5.0% by mass, in terms of the oxide. If the amount of phosphorous supported is less than 0.5% by mass, an effect of phosphorous cannot be exhibited sufficiently, and if it is more than 10% by mass, the acidic property of the catalyst becomes strong and a cracking reaction may occur. A method of making phosphorous be supported on the support is not particularly limited, and phosphorous may be supported by coexisting in an aqueous solution containing the above-described metals of groups 8 to 10 and metals of group 6 of the periodic table and may be successively supported before supporting a metal or after supporting a metal.

The method for incorporating these active metals into the catalyst is not especially limited. A known method that is applied when producing a general hydrocracking catalyst may be employed. Generally, it is preferred to employ a method in which a solution containing a salt of the active metal is impregnated into the catalyst support. In addition, an equilibrium adsorption method, a pore-filling method, an incipient-wetness method and the like can also be preferably employed. For example, a pore-filling method is a method in which the pore volume of a support is measured in advance and then the support is impregnated with the same volume of a metal salt solution. In addition, the impregnation method is not especially limited. The support may be impregnated by a suitable method based on the amount of the metal supported and the physical properties of the catalyst support.

In the present embodiment, the number of the hydrocracking catalyst A-2 types to be used is not especially limited. For example, one type of catalyst may be used singly or a plurality of catalysts with different active metal species or support constituent components may be used. Examples of a suitable combination when using a plurality of different catalysts include a catalyst containing cobalt-molybdenum following on from a catalyst containing nickel-molybdenum, a catalyst containing nickel-cobalt-molybdenum following on from a catalyst containing nickel-molybdenum, a catalyst containing nickel-cobalt-molybdenum following on from a catalyst containing nickel-tungsten, and a catalyst containing cobalt-molybdenum following on from a catalyst containing nickel-cobalt-molybdenum. Prior to and/or following these combinations, a nickel-molybdenum catalyst may be further combined.

When combining a plurality of catalysts with different support components, a catalyst may be used that, for example, has an aluminum oxide content in the range of 80 to 99% by mass following on from a catalyst having an aluminum oxide content of 30% by mass or more and less than 80% by mass based on the total mass of the support.

Further, other than the hydrocracking catalyst A-2, a guard catalyst, a demetallization catalyst, and an inactive filler may optionally be used for the purpose of trapping the scale content which flows in along with the pre-treated hydrocarbon oil fraction and supporting the hydrocracking catalyst A-2 at the partition part of the catalyst bed as necessary. These may be used singly or in combinations thereof.

It is preferred that the pore volume of the hydrocracking catalyst A-2 as measured by a nitrogen adsorption BET method is 0.30 to 0.85 mL/g, and more preferred is 0.45 to 0.80 mL/g. If the pore volume is less than 0.30 mL/g, the dispersibility of the supported metals is insufficient, and the active sites may decrease. In addition, if the pore volume is more than 0.85 mL/g, the catalyst strength is insufficient, so that the catalyst may turn into a powder and break up during use.

Further, it is preferred that the average pore size of the catalyst determined by a nitrogen adsorption BET method is 5 to 11 nm, and more preferred is 6 to 9 nm. If the average pore size is less than 5 nm, the reaction substrate is not sufficiently dispersed in the pores, and the reactivity may decrease. In addition, if the average pore size is more than 11 nm, the pore surface area decreases and the activity may become insufficient.

In addition, in the hydrocracking catalyst A-2, in order to maintain effective catalyst pores and exhibit sufficient activity, it is preferred that the ratio of the pore volume derived from pores having a pore diameter of 3 nm or less to the total pore volume is 35% by volume or less.

When the hydrocracking catalyst A-2 is used, the hydrocracking conditions can be set to, for example, a hydrogen pressure of 2 to 13 MPa, a liquid hourly space velocity (LHSV) of 0.1 to 3.0 $h^{-1}$, and a hydrogen-oil ratio (hydrogen/oil ratio) of 150 to 1,500 $Nm^3/m^3$, are preferably a hydrogen pressure of 4.5 to 12 MPa, a liquid hourly space velocity of 0.3 to 1.5 $h^{-1}$, and a hydrogen-oil ratio of 380 to 1,200 $Nm^3/m^3$, and more preferably a hydrogen pressure of 6 to 15 MPa, a liquid hourly space velocity of 0.3 to 1.5 $h^{-1}$, and a hydrogen-oil ratio of 350 to 1,000 $Nm^3/m^3$. All of these conditions are factors having an influence on the reaction activity. For example, if the hydrogen pressure and the hydrogen-oil ratio are less than the above lower limits, the reactivity tends to decrease and the activity tends to rapidly decrease. On the other hand, if the hydrogen pressure and the hydrogen-oil ratio are more than the above upper limits, an excessive investment in equipment such as a compressor tends to be required. In addition, the lower the liquid hourly space velocity is, the more advantageous it tends to be for the reaction. However, if the liquid hourly space velocity is less than the above lower limit, a reactor having an extremely large internal volume is required and an excessive investment in equipment tends to be required. On the other hand, if the liquid hourly space velocity is more than the above upper limit, the reaction tends not to sufficiently proceed. Further, the reaction temperature may be 180 to 400° C., is preferably 200 to 370° C., more preferably 250 to 350° C., and especially preferably 280 to 350° C. If the reaction temperature is more than 400° C., not only does the yield of the pre-treated hydrocarbon oil fraction decrease due to the base oil fraction being broken down into a light fraction, but the generated product is colored, so that usage as a fuel oil base tends to be limited. On the other hand, if the reaction temperature is less than 180° C., the hydrocracking reaction does not proceed sufficiently, so that the yield of the pre-treated hydrocarbon oil fraction decreases.

<Hydroisomerization Treatment>

The hydroisomerization treatment can be performed by, in the presence of hydrogen, bringing the hydrocarbon oil into contact with a hydroisomerization catalyst. As the hydrocarbon oil, a light FT synthetic oil or the like can be used. The light FT synthetic oil means an FT synthetic oil having a boiling point range of 330 to 520° C. The hydroisomerization treatment herein includes, in addition to isomerization of a normal paraffin into an isoparaffin, conversion of an olefin into a paraffin by hydrogenation and conversion of an alcohol into a paraffin by dehydroxylation. It is preferable that, as the hydroisomerization catalyst, a catalyst in which one or more metals selected from the group consisting of metals of group 9 and group 10 of the periodic table as an active metal are supported on a support containing a solid acid (hereinafter, referred to as "hydroisomerization catalyst B") be used.

In the support containing a solid acid of the hydroisomerization catalyst B, examples of the solid acid include amorphous metal oxides having heat resistance, such as silica-alumina, silica-zirconia, and alumina-boria.

The support containing a solid acid in the hydroisomerization catalyst B can be produced by extruding and then calcining a mixture containing the above-described solid acid and a binder. The blending ratio of the solid acid is preferably 1 to 70% by mass, and more preferably 2 to 60% by mass based on the total amount of the support. As the binder, although not particularly limited, alumina, silica, silica-alumina, titania, and magnesia are preferable, and alumina is more preferable. The blending ratio of the binder is preferably 30 to 99% by mass, and more preferably 40 to 98% by mass based on the total amount of the support.

The calcining temperature of the above-described mixture is preferably 400 to 550° C., more preferably 470 to 530° C., and further preferably 490 to 530° C.

Specific examples of the metal of group 9 and group 10 of the periodic table in the hydroisomerization catalyst B include cobalt, nickel, rhodium, palladium, iridium, and platinum. It is preferable that, among them, one or more metals selected from nickel, palladium, and platinum be used. These metals can be supported on the above-described support by conventional methods such as impregnation and ion exchange. Although the amount of the supported metal is not particularly limited, it is preferable that the total amount of the metal be 0.1 to 3.0% by mass with respect to the support.

Reaction conditions when using the hydroisomerization catalyst B are not particularly limited as long as a pre-treated hydrocarbon oil in which the isomer ratio of the carbon number 18 is 92 to 98% by mass can be obtained. For example, the following reaction conditions are appropriately selected to be performed.

The hydrogen partial pressure when using the hydroisomerization catalyst B is preferably 0.5 to 12 MPa, and more preferably 1.0 to 5.0 MPa. The liquid hourly space velocity (LHSV) of a middle fraction is preferably 0.1 to 10.0 h$^{-1}$, and more preferably 0.3 to 3.5 h$^{-1}$. The hydrogen/oil ratio is preferably 50 to 1000 NL/L, and more preferably 70 to 800 NL/L.

In the present specification, "LHSV (liquid hourly space velocity)" means a volume flow of a hydrocarbon oil in the standard state (25° C., 101325 Pa) per volume of a catalyst layer filled with a catalyst, and the unit "h$^{-1}$" indicates the reciprocal of hour. In addition, "NL" that is the unit of hydrogen volume in the hydrogen/oil ratio indicates hydrogen volume (L) in the normal state (0° C., 101325 Pa).

It is preferable that the reaction temperature when using the hydroisomerization catalyst B be set such that a pre-treated hydrocarbon oil in which the ratio of a branched paraffin having a carbon number of 18 to a hydrocarbon having a carbon number of 18 is 85 to 98% by mass is obtained. For example, examples thereof include 200 to 370° C., and more preferably 320 to 350° C. so as to improve a low-temperature property. If the reaction temperature is more than 370° C., a side reaction for cracking to a light component is increased and the yield of a middle fraction is decreased, and furthermore, the pre-treated hydrocarbon oil is colored and the usage is limited. If the reaction temperature is less than 200° C., an alcohol component cannot be completely removed and tends to remain.

(Raw Material Distillation Step)

In the raw material distillation step, an oil fraction to be treated containing a hydrocrackate (for example, hydrocarbon having a carbon number of less than 30) and a heavy fraction that contains a heavy component and is heavier than an oil component to be treated are respectively fractionated from the pre-treated hydrocarbon oil obtained in the pre-treatment step. In addition, in some cases, light fractions such as gas, naphtha, and kerosene and gas oil or the like are further fractionated.

The oil fraction to be treated is a fraction for obtaining a lubricating base oil through a first step and a second step described below (and, if necessary, a hydrorefining step and a product distillation step), and the boiling point range thereof can be appropriately changed based on an intended product.

The oil fraction to be treated is preferably a fraction having a 10% by volume distillation temperature of 320° C. or more and a 90% by volume distillation temperature of 540° C. or less. By making the oil fraction to be treated be a fraction having the boiling point range within the above-described range, a useful lubricating base oil can be produced more efficiently. The 10% by volume distillation temperature and the 90% by volume distillation temperature are values measured based on JIS K2254 "Petroleum products-Determination of distillation characteristics-Gas chromatographic method".

The heavy fraction is a heavier fraction having a boiling point higher than the oil fraction to be treated. That is, the heavy fraction is a fraction having a 10% by volume distillation temperature higher than the 90% by volume distillation temperature of the oil fraction to be treated, and is, for example, a fraction having a 10% by volume distillation temperature higher than 520° C.

In some cases, the pre-treated hydrocarbon oil contains a lighter fraction having a boiling point lower than the oil fraction to be treated (light fraction) other than the oil fraction to be treated and the heavy fraction. The light fraction is a fraction having a 90% by volume distillation temperature lower than the 10% by volume distillation temperature of the oil fraction to be treated, and is, for example, a fraction having a 90% by volume distillation temperature lower than 320° C.

Distillation conditions in the raw material distillation step are not particularly limited as long as they are conditions capable of fractionating the oil fraction to be treated and the heavy fraction respectively from the pre-treated hydrocarbon oil. For example, the raw material distillation step may be a step of fractionating the oil fraction to be treated and the heavy fraction from the pre-treated hydrocarbon oil by vacuum distillation, or may be a step of fractionating the oil fraction to be treated and the heavy fraction from the pre-treated hydrocarbon oil by combining atmospheric distillation (or distillation under pressure) and vacuum distillation.

For example, in the case where the pre-treated hydrocarbon oil contains the light fraction, the raw material distillation step can be performed by atmospheric distillation (or distillation under pressure) for distilling away the light fraction from the pre-treated hydrocarbon oil and vacuum distillation for fractionating the oil fraction to be treated and the heavy fraction respectively from a bottom oil of the atmospheric distillation.

In the raw material distillation step, the oil fraction to be treated may be fractionated as a single fraction, or may be fractionated as a plurality of fractions in accordance with desirable lubricating base oil. The plurality of oil fractions to be treated, which is fractionated in this manner, can each be independently subjected to the first step and the second step described above. Moreover, a part or all of the plurality of oil fractions to be treated can be mixed and subjected to the first step and the second step described above.

(First Step)

In the first step, a $^{13}$C-NMR analysis is performed with respect to an oil to be treated containing a normal paraffin and an isoparaffin, and the oil to be treated is selected based on the above-described index values (1), (2) and (3) in an obtained $^{13}$C-NMR spectrum.

In the first step, the criterion of selecting based on the index values (1), (2) and (3) can be appropriately determined in accordance with a treatment condition of isomerization dewaxing, characteristics of an intended lubricating base oil (dewaxed oil) and the like.

In the case where the second step described below is a step of performing isomerization dewaxing of the oil to be treated at a reaction temperature of 280 to 360° C., it is preferable that the first step be a step of selecting the oil to be treated having the index value (1) of 0.01 to 0.1, and more preferably 0.01 to 0.08, the index value (2) of 0.2 to 0.6, and more preferably 0.25 to 0.55, and the index value (3) of 0.05 to 0.2, and more preferably 0.05 to 0.18.

In the first step, in addition to the above-described index values (1), (2) and (3), the oil to be treated may be selected based on the following index values (4) and (5), index value (4): an average carbon number determined from a gas chromatography analysis of the oil to be treated, and index value (5): a product of the index value (2) and the index value (4) of the oil to be treated.

Here, the average carbon number is determined from a gas chromatography analysis. Specifically, a gas chromatography analysis of a lubricating base oil is performed, and with reference to gas chromatogram of a normal paraffin mixture, which is measured under the same conditions, the carbon number distribution and the component ratio of each carbon number of the lubricating base oil are measured. The sum of a product of the component ratio of each carbon number and the carbon number is determined from the result, and this is defined as the average carbon number. Regarding the gas chromatography analysis, the measurement can be performed, for example, under the following conditions, by using GC-2010 manufactured by Shimadzu Corporation. Column: UltraALLOY-1HT (30 m×0.25 mmφ), Carrier Gas: He 200 kPa, Detector: FID, Detector Temperature: 350° C., Column Oven Temperature: 50° C. to 320° C., Column Temperature Increase Rate: 6° C./min, Injector Volume: 0.4 µL (split ratio 70/1).

The index value (5) indicates the carbon number constituting the hydrocarbon main chain of the oil to be treated. When the index value (5) becomes large, the viscosity index of the intended lubricating base oil becomes large, but cold flow property tends to be deteriorated. When the index value (5) becomes small, while the viscosity index becomes small, cold flow property tends to be improved. Therefore, if the index values (4) and (5) are values within a preferred range described below in accordance with the intended lubricating base oil, a lubricating base oil that is within desirable kinematic viscosity range and satisfies superior cold flow property can be obtained.

For example, in the case where the intended lubricating base oil corresponds to 70 Pale (fraction mainly having boiling point range of 330 to 410° C.) and SAE-10 (fraction mainly having boiling point range of 410 to 460° C.) and the second step is a step of performing isomerization dewaxing of the oil to be treated at a reaction temperature of 280 to 360° C., the oil to be treated selected in the first step has the index value (4) of 23 or more and less than 29, preferably satisfies a condition that the index value (5) is 5 to 19, and more preferably satisfies a condition that the index value (5) is 6 to 17.

Moreover, in the case where the intended lubricating base oil corresponds to SAE-20 (fraction mainly having boiling point range of 460 to 520° C.) and the second step is a step of performing isomerization dewaxing of the oil to be treated at a reaction temperature of 280 to 360° C., the oil to be treated selected in the first step has the index value (4) of 31 or more and less than 35, preferably satisfies a condition that the index value (5) is 8 to 25, and more preferably satisfies a condition that the index value (5) is 10 to 20.

(Second Step)

In the second step, a dewaxed oil is obtained by isomerization dewaxing of the oil to be treated selected in the first step. The isomerization dewaxing is carried out by, in the presence of hydrogen, bringing the oil to be treated into contact with an isomerization dewaxing catalyst.

<Isomerization Dewaxing Catalyst>

As the isomerization dewaxing catalyst, a catalyst that is generally used for isomerization dewaxing, namely, a catalyst in which a metal having a hydrogenation activity is supported on an inorganic support or the like, can be used.

As the metal having a hydrogenation activity in the isomerization dewaxing catalyst, one or more metals selected from the group consisting of metals of group 6, group 8, group 9, and group 10 of the periodic table are used. Specific examples of these metals include noble metals such as platinum, palladium, rhodium, ruthenium, iridium, and osmium, or cobalt, nickel, molybdenum, tungsten, and iron. Preferred are platinum, palladium, nickel, cobalt, molybdenum, and tungsten, and more preferred are platinum and palladium. In addition, it is also preferred to use these metals in combinations of a plurality of species. In this case, examples of preferred combinations include platinum-palladium, cobalt-molybdenum, nickel-molybdenum, nickel-cobalt-molybdenum, and nickel-tungsten. Here, the periodic table means a long-form periodic table of elements based on the rules of IUPAC (International Union of Pure and Applied Chemistry).

Examples of inorganic supports constituting the isomerization dewaxing catalyst include metal oxides such as alumina, silica, titania, zirconia, and boria. These metal oxides may be one kind, a mixture of two or more kinds, or a composite metal oxide such as silica-alumina, silica-zirconia, alumina-zirconia, and alumina-boria. From the perspective of efficiently promoting the isomerization of normal paraffins, the inorganic support is preferably a composite metal oxide that is a solid acid, such as silica-alumina, silica-zirconia, alumina-zirconia, and alumina-boria. Further, a small amount of zeolite may be included in the inorganic support. In order to improve the extrudability and mechanical strength of the support, the inorganic support may be blended with a binder. Examples of preferred binders include alumina, silica, and magnesia.

As the content of the metal having a hydrogenation activity in the isomerization dewaxing catalyst, if this metal is the above-described noble metal, it is preferred that the content is about 0.1 to 3% by mass based on the mass of the support as metal atoms. Further, if this metal is a metal other than the above-described noble metals, it is preferred that the content is about 2 to 50% by mass based on the mass of the support as a metal oxide. If the content of the metal having a hydrogenation activity is less than the above-described lower limit, isomerization tends not to proceed sufficiently.

On the other hand, if the content of the metal having a hydrogenation activity is more than the above-described upper limit, dispersity of the metal having a hydrogenation activity deteriorates, so that the activity of the catalyst tends to decrease, and the catalyst cost increases.

Further, the isomerization dewaxing catalyst may be a catalyst in which one or more metals selected from the elements of metals of group 6, group 8, group 9, and group 10 of the periodic table that is supported on a support including a porous inorganic oxide that is formed from a substance selected from aluminum, silicon, zirconium, boron, titanium, magnesium, and zeolite.

Examples of the porous inorganic oxide used as a support of such an isomerization dewaxing catalyst include alumina, silica, titania, zirconia, boria, and zeolite, and a complex oxide formed from alumina and at least one of silica, titania, zirconia, boria, and silica and zeolite is preferable. Although a method for producing such a porous inorganic oxide is not particularly limited, a sol-gel method or the like can be employed. In the complex oxide formed from alumina and another oxide, the content of alumina is preferably 10% by mass or more, and more preferably 20% by mass or more. Moreover, it is preferably 90% by mass or less, more preferably 60% by mass or less, and further preferably 40% by mass or less.

Examples of the zeolite, which is a crystalline alumino silicate, include faujasite, pentasil, mordenite, TON, MTT, and *MRE. A zeolite that has been ultrastabilized by a predetermined hydrothermal treatment and/or acid treatment, or a zeolite whose alumina content has been adjusted may be used. It is preferred to use faujasite or mordenite, and among these, especially preferred to use a Y or beta type. The Y type is preferably further ultrastabilized. A zeolite ultrastabilized by a hydrothermal treatment has, in addition to its inherent pore structure, called micropores, of 2 nm or less, newly formed pores in the range of 2 to 10 nm. The hydrothermal treatment may be carried out under known conditions.

For any of the above-described isomerization dewaxing catalysts, the method for supporting the active metal on the support is not especially limited. A known method that is applied when producing a general isomerization dewaxing catalyst may be employed. Generally, it is preferred to employ a method in which a solution containing a salt of the active metal is impregnated into the catalyst support. In addition, an equilibrium adsorption method, a pore-filling method, an incipient-wetness method and the like can also be preferably employed. For example, a pore-filling method is a method in which the pore volume of a support is measured in advance and then the support is impregnated with the same volume of a metal salt solution. Although the impregnation method is not especially limited, the support may be impregnated by a suitable method based on the amount of the metal supported and the physical properties of the catalyst support.

As the isomerization dewaxing catalyst, the following isomerization dewaxing catalyst C can also be used.

The isomerization dewaxing catalyst C is imparted with its characteristics as a result of being produced by a specific method. The isomerization dewaxing catalyst C will now be described with reference to a preferred production aspect thereof.

The method for producing the isomerization dewaxing catalyst C includes a first step of obtaining a support precursor by heating a mixture that includes an ion-exchanged zeolite obtained by ion-exchanging an organic template-containing zeolite that contains an organic template and has a one-dimensional, 10-membered ring pore structure in a solution containing ammonium ions and/or protons, and a binder, in a $N_2$ atmosphere at a temperature of 250 to 300° C., and a second step of obtaining an isomerization dewaxing catalyst in which platinum and/or palladium is supported on a support including zeolite by calcining a catalyst precursor incorporating a platinum salt and/or palladium salt in the support precursor in an atmosphere containing molecular oxygen at a temperature of 350 to 400° C.

From the perspective of achieving a high level of both high isomerization activity and suppressed cracking activity in the isomerization dewaxing reactions of normal paraffins, the organic template-containing zeolite used in the isomerization dewaxing catalyst C has a one-dimensional pore structure formed from a 10-membered ring. Examples of such zeolites include AEL, EUO, FER, FEU, MEL, MFI, NES, TON, MTT, WET, *MRE, and SSZ-32. The above three-lettered acronyms represent framework-type codes assigned to various structures of classified molecular sieve-type zeolites by the Structure Commission of the International Zeolite Association. It is also noted that zeolites having the same topology are collectively designated by the same code.

Among the above-described zeolites having a one-dimensional, 10-membered ring pore structure, from the perspective of high isomerization activity and low cracking activity, preferred as the organic template-containing zeolite are zeolites having a TON or an MTT structure, zeolite ZSM-48, which is a zeolite having a *MRE structure, and zeolite SSZ-32. Zeolite ZSM-22 is more preferred among zeolites having the TON structure, and zeolite ZSM-23 is more preferred among zeolites having the MTT structure.

The organic template-containing zeolite is hydrothermally synthesized according to a known method from a silica source, an alumina source, and an organic template that is added to build the above-described predetermined pore structure.

The organic template is an organic compound having an amino group, an ammonium group and the like, and is selected according to the structure of the zeolite to be synthesized. However, it is preferred that the organic template is an amine derivative having an amino group. Specifically, the organic template is preferably at least one selected from the group consisting of alkylamines, alkyldiamines, allcyltriamines, alkyltetramines, pyrrolidine, piperazine, aminopiperazine, alkylpentamines, alkylhexamines, and their derivatives. Examples of the carbon number of the above-described alkyls include 4 to 10, and it is preferably 6 to 8. In addition, examples of typical alkyldiamines include 1,6-hexanediamine and 1,8-diaminooctane.

The molar ratio of the silicon element to aluminum element ([Si]/[Al], hereinafter referred to as a "Si/Al ratio") that constitute the organic template-containing zeolite having a one-dimensional, 10-membered ring pore structure is preferably 10 to 400, and more preferably 20 to 350. If the Si/Al ratio is less than 10, although the activity for the conversion of normal paraffins increases, the isomerization selectivity to isoparaffins decreases, and cracking reactions caused by an increase in the reaction temperature tend to sharply increase, which is undesirable. Conversely, if the Si/Al ratio is more than 400, the catalytic activity needed for the conversion of normal paraffins cannot be easily obtained, which is undesirable.

The synthesized organic template-containing zeolite, which has preferably been washed and dried, typically has alkali metal cations as counter cations, and incorporates the organic template in its pore structure. The zeolite containing an organic template, which is used for producing the isomerization dewaxing catalyst C, is preferably in such a synthesized state, i.e., preferably, the zeolite has not been subjected to a calcining treatment for removing the organic template incorporated therein.

The organic template-containing zeolite is next ion-exchanged in a solution containing ammonium ions and/or protons. By the ion-exchange treatment, the counter cations contained in the organic template-containing zeolite are exchanged for ammonium ions and/or protons. Further, at the same time, a portion of the organic template incorporated in the organic template-containing zeolite is removed.

The solution used for the ion-exchange treatment is preferably a solution that uses a solvent containing at least 50% by volume of water, and more preferably is an aqueous solution. Examples of compounds for supplying ammonium ions into the solution include various inorganic and organic ammonium salts, such as ammonium chloride, ammonium sulfate, ammonium nitrate, ammonium phosphate, and ammonium acetate. On the other hand, mineral acids such as hydrochloric acid, sulfuric acid, and nitric acid are typically used as compounds for supplying protons into the solution. The ion-exchanged zeolite (here, an ammonium-form zeolite) obtained by ion exchange of the organic template-containing zeolite in the presence of ammonium ions releases ammonia during subsequent calcination, and the counter cations are converted into protons to form Bronsted acid sites. Ammonium ions are preferred as the cationic species used for the ion exchange. The amount of ammonium ions and/or protons contained in the solution is preferably set to 10 to 1,000 equivalents based on the total amount of the counter cations and organic template contained in the organic template-containing zeolite used.

The ion-exchange treatment may be performed on the organic template-containing zeolite in powder form, or alternatively, prior to the ion-exchange treatment, the organic template-containing zeolite may be blended with an inorganic oxide, which is a binder, and extruded, and the ion-exchange treatment may be performed on the resulting extruded body. However, if the extruded body is subjected to the ion-exchange treatment in an uncalcined state, problems such as the extruded body collapsing and turning into a powder tend to occur. Therefore, it is preferred to subject the organic template-containing zeolite in powder form to an ion-exchange treatment.

The ion-exchange treatment is preferably performed based on a standard method, i.e., a method in which the zeolite containing an organic template is dipped in a solution, preferably an aqueous solution, containing ammonium ions and/or protons, and the solution is stirred or fluidized. It is preferred to perform the stirring or fluidization under heating to increase the ion-exchange efficiency. In the present aspect, especially preferred is a method in which the aqueous solution is heated, boiled, and ion-exchanged under reflux.

Further, from the perspective of increasing the ion-exchange efficiency, during the ion exchange of the zeolite in a solution, it is preferred to exchange the solution with a fresh one once or twice or more, and more preferably exchanged with a fresh one once or twice. When exchanging the solution once, the ion-exchange efficiency can be improved by, for example, dipping the organic template-containing zeolite in a solution containing ammonium ions and/or protons, and heating the solution under reflux for 1 to 6 hours, followed by exchanging the solution with a fresh one, and further heating under reflux for 6 to 12 hours.

By the ion-exchange treatment, substantially all of the counter cations such as an alkali metal in the zeolite can be exchanged for ammonium ions and/or protons. On the other hand, regarding the organic template incorporated in the zeolite, although a portion of the organic template is removed by the ion-exchange treatment, it is generally difficult to remove all of the organic template even if the ion-exchange treatment is repeatedly performed, so that a portion of the organic template remains inside the zeolite.

In the isomerization dewaxing catalyst C, a support precursor is obtained by heating a mixture in which the ion-exchanged zeolite and the binder are included in a nitrogen atmosphere at a temperature of 250 to 350° C.

The mixture in which the ion-exchanged zeolite and the binder are included is preferably obtained by blending an inorganic oxide, which is a binder, with the ion-exchanged zeolite obtained by the above-described method, and extruding the resulting composition to form a extruded body. The purpose of blending an inorganic oxide with the ion-exchanged zeolite is to increase the mechanical strength of the support (in particular, a particulate support) obtained by calcining the extruded body to a degree that can withstand practical applications. However, the present inventor found that the selection of the type of inorganic oxide affects the isomerization selectivity of the isomerization dewaxing catalyst. From this perspective, at least one inorganic oxide selected from alumina, silica, titania, boria, zirconia, magnesia, ceria, zinc oxide, phosphorus oxide, and a composite oxide containing a combination of two or more of these oxides can be used as the inorganic oxide. Among the above, silica and alumina are preferred, and alumina is more preferred, from the perspective of further improving the isomerization selectivity of the isomerization dewaxing catalyst. The phrase "composite oxide containing a combination of two or more of these oxides" refers to a composite oxide containing at least two components from alumina, silica, titania, boria, zirconia, magnesia, ceria, zinc oxide, and phosphorus oxide, but is preferably an alumina-based composite oxide containing 50% by mass or more of an alumina component based on the composite oxide, and among those, is more preferably alumina-silica.

The blending ratio of the ion-exchanged zeolite and the inorganic oxide in the above-described composition is preferably 10:90 to 90:10, and more preferably 30:70 to 85:15, in terms of the mass ratio of the ion-exchanged zeolite to the inorganic oxide. If this ratio is less than 10:90, the activity of the isomerization dewaxing catalyst tends to be insufficient, which is undesirable. Conversely, if the ratio is more than 90:10, the mechanical strength of the support obtained by extruding and calcining the composition tends to be insufficient, which is undesirable.

Although the method for blending the inorganic oxide with the ion-exchanged zeolite is not especially limited, a general method can be employed, such as, for example, a method in which a suitable amount of a liquid such as water is added to the powders of both components to form a viscous fluid, and the fluid is kneaded in a kneader or the like.

The composition containing the ion-exchanged zeolite and inorganic oxide, or a viscous fluid including the composition, is extruded by a method such as extrusion molding, and is preferably dried, to form a particulate extruded body. Although the shape of the extruded body is not especially limited, examples of the shape include a cylindrical shape, a pellet shape, a spherical shape, and an irregular tubular shape having a three leaf shaped or a four leaf shaped cross-section. Although the size of the extruded body is not especially limited, the extruded body is preferably, for example, about 1 to 30 mm in the long axis, and about 1 to 20 mm in the short axis, from the perspective of the ease of handling, the load density in the reactor and the like.

In the isomerization dewaxing catalyst C, it is preferred to form the support precursor by drying enough the thus-obtained extruded body at 100° C. or less, and then heating in a $N_2$ atmosphere at a temperature of 250 to 350° C. Regarding the heating time, preferred is 0.5 to 10 hours, and more preferred is 1 to 5 hours.

In the isomerization dewaxing catalyst C, if the above-described heating temperature is less than 250° C., a large amount of organic template remains, and the zeolite pores become blocked with the remaining template. The isomerization active sites are thought to exist near the pore mouth. Thus, in the above case, the reaction substrate cannot disperse into the pores due to the pore blockage, so that the active sites become covered, the isomerization reaction does not easily proceed, and a normal paraffin conversion rate tends not to be sufficiently obtained. On the other hand, if the heating temperature is more than 350° C., the isomerization selectivity of the obtained isomerization dewaxing catalyst does not sufficiently improve.

It is preferred that the lower limit for the temperature when forming the support precursor by heating the extruded body is 280° C. or more, and that the upper limit for the temperature is 330° C. or less.

In the isomerization dewaxing catalyst C, it is preferred to heat the above-described mixture so that a portion of the organic template included in the extruded body remains. Specifically, it is preferable that the heating conditions be set such that the amount of carbon of the isomerization dewaxing catalyst obtained through calcining after metal supporting described below is 0.4 to 3.5% by mass (preferably 0.4 to 3.0% by mass, more preferably 0.4 to 2.5% by mass, and further preferably 0.4 to 1.5% by mass) or the micropore volume per unit mass of the catalyst is 0.02 to 0.12 cm$^3$/g and the micropore volume per unit mass of zeolite contained in the catalyst is 0.01 to 0.12 cm$^3$/g.

Next, the catalyst precursor incorporating a platinum salt and/or palladium salt in the above-described support precursor is calcined in an atmosphere containing molecular oxygen at a temperature of 250 to 400° C., preferably 280 to 400° C., and more preferably 300 to 400° C., to obtain an isomerization dewaxing catalyst C in which a platinum and/or palladium is supported on a support including zeolite. Here, "in an atmosphere containing molecular oxygen" means bringing into contact with a gas including oxygen gas, and of those preferably air. The calcining time is preferably 0.5 to 10 hours, and more preferably 1 to 5 hours.

Examples of the platinum salt include chloroplatinic acid, tetraammineplatinum dinitrate, dinitroaminoplatinum, and tetraamminedichloroplatinum. Since chloride salts can produce hydrochloric acid during a reaction, which may cause apparatus corrosion, tetraammineplatinum dinitrate, which is a platinum salt that is not a chloride salt and in which a high level of platinum is dispersed, is preferred.

Examples of the palladium salt include palladium chloride, tetraammine palladium nitrate, and diaminopalladium nitrate. Since chloride salts can produce hydrochloric acid during a reaction, which may cause apparatus corrosion, tetraammine palladium nitrate, which is a palladium salt that is not a chloride salt and in which a high level of palladium is dispersed, is preferred.

The amount of the active metal supported on the support including zeolite according to the isomerization dewaxing catalyst C is preferably 0.001 to 20% by mass, and more preferably 0.01 to 5% by mass, based on the mass of the support. If the amount supported is less than 0.001% by mass, it is difficult to impart a predetermined hydrogenation/dehydrogenation function to the catalyst. Conversely, if the amount supported is more than 20% by mass, conversion on the active metal of hydrocarbons into lighter products by cracking tends to proceed, so that the yield of the intended fraction tends to decrease, and the catalyst costs tend to increase, which are undesirable.

Further, when the isomerization dewaxing catalyst C is used for isomerization dewaxing of a hydrocarbon oil containing many sulfur-containing compounds and/or nitrogen-containing compounds, from the perspective of the durability of catalytic activity, it is preferred that the active metals are a combination such as nickel-cobalt, nickel-molybdenum, cobalt-molybdenum, nickel-molybdenum-cobalt, or nickel-tungsten-cobalt. It is preferred that the amount of these metals supported is 0.001 to 50% by mass, and more preferably 0.01 to 30% by mass, based on the mass of the support.

In the isomerization dewaxing catalyst C, it is preferred to calcine the above-described catalyst precursor so that the organic template remaining in the support precursor remains. Specifically, it is preferable that the heating conditions be set such that the amount of carbon of the isomerization dewaxing catalyst obtained is 0.4 to 3.5% by mass (preferably 0.4 to 3.0% by mass, more preferably 0.4 to 2.5% by mass, and further preferably 0.4 to 1.5% by mass) or the micropore volume per unit mass of the isomerization dewaxing catalyst C obtained is 0.02 to 0.12 cm$^3$/g and the micropore volume per unit mass of zeolite contained in the catalyst is 0.01 to 0.12 cm$^3$/g.

In the present specification, the amount of carbon of the isomerization dewaxing catalyst C can be analyzed by a combustion in oxygen flow-infrared absorption method. Specifically, it can be determined by burning the catalyst in the oxygen flow and performing quantitation of the amount of carbon by the infrared absorption method, using a carbon/sulfur analyzer (for example, EMIA-920V manufactured by HORIBA, Ltd.).

The micropore volume per unit mass of the isomerization dewaxing catalyst C is calculated by a method called nitrogen adsorption measurement. Namely, for the catalyst, the micropore volume per unit mass of the catalyst is calculated by analyzing a physical adsorption and desorption isotherm of nitrogen measured at the temperature of liquid nitrogen (−196° C.), specifically, analyzing an adsorption isotherm of nitrogen measured at the temperature of liquid nitrogen (−196° C.) by a t-plot method. Further, the micropore volume per unit mass of the zeolite contained in the catalyst is also calculated by the above-described nitrogen adsorption measurement.

A micropore volume $V_z$ per unit mass of the zeolite contained in the isomerization dewaxing catalyst C can be calculated, for example, if the binder does not have a micropore volume, based on the following expression from a value $V_c$ of the micropore volume per unit mass of the isomerization dewaxing catalyst C and the content $M_z$ (% by mass) of zeolite in the catalyst.

$$V_z = V_c/M_z \times 100$$

It is preferred that, subsequent to the calcination treatment, the isomerization dewaxing catalyst C is subjected to a reduction treatment after the catalyst is loaded in the reactor for conducting the isomerization dewaxing reaction. Specifically, it is preferred that the hydroisomerization catalyst is subjected to the hydrogen reduction treatment for about 0.5 to 10 hours in an atmosphere containing molecular hydrogen, and preferably under a stream of hydrogen gas, preferably at 250 to 500° C., and more preferably at 300 to 400° C. By performing this step, it can be further ensured that high activity for the dewaxing of the hydrocarbon oil can be imparted to the catalyst.

The isomerization dewaxing catalyst C is a hydroisomerization catalyst containing a support that includes a zeolite having a one-dimensional, 10-membered ring pore structure and a binder, and platinum and/or palladium supported on the support. The isomerization dewaxing catalyst according to the present aspect is a catalyst in which the amount of carbon is 0.4 to 3.5% by mass. Moreover, the isomerization dewaxing catalyst according to the present aspect is an isomerization dewaxing catalyst in which the micropore volume per unit mass is 0.02 to 0.12 cm$^3$/g. Further, this zeolite is preferably a zeolite derived from ion-exchanged zeolite obtained by ion-exchanging an organic template-containing zeolite that contains an organic template and has a one-dimensional, 10-membered ring pore structure in a solution containing ammonium ions and/or protons, in which the micropore volume per unit mass of the zeolite contained in the catalyst is 0.01 to 0.12 cm$^3$/g.

The isomerization dewaxing catalyst C can be produced by the method described above. The amount of carbon and the micropore volume per unit mass of the catalyst and the micropore volume per unit mass of the zeolite contained in the catalyst can be set to be within the above-described ranges by appropriately adjusting the amount of ion-exchanged zeolite blended in the mixture including the ion-exchanged zeolite and a binder, the heating conditions of the mixture in a N$_2$ atmosphere, and the heating conditions of the catalyst precursor in the atmosphere containing molecular oxygen.

<Reaction Conditions in the Second Step>

In the second step, the reaction temperature of the isomerization dewaxing is preferably 280 to 360° C., and more preferably 300 to 340° C. If the reaction temperature is less than 280° C., the isomerization of the normal paraffins contained in the oil to be treated tends not to easily proceed, so that the reduction and removal of the wax component tend to be insufficient. Conversely, if the reaction temperature is more than 360° C., cracking of the oil to be treated is significant, so that the yield of the lubricating base oil tends to decrease.

The reaction pressure in the isomerization dewaxing is preferably 0.1 to 20 MPa, and more preferably 0.5 to 15 MPa. If the reaction pressure is less than 0.1 MPa, catalyst degradation due to the formation of coke tends to be accelerated. Conversely, if the reaction pressure is more than 20 MPa, construction costs for the apparatus increase, so that it tends to become difficult to realize an economical process.

The liquid hourly space velocity of the oil to be treated based on the catalyst in the isomerization dewaxing is preferably 0.01 to 100 h$^{-1}$, and more preferably 0.1 to 50 h$^{-1}$. If the liquid hourly space velocity is less than 0.01 h$^{-1}$, the cracking of the oil to be treated tends to proceed excessively, so that production efficiency tends to decrease. Conversely, if the liquid hourly space velocity is more than 100 h$^{-1}$, the isomerization of the normal paraffins contained in the oil to be treated tends not to proceed easily, so that the reduction and removal of the wax component tend to be insufficient.

The supply ratio of hydrogen to oil to be treated in the isomerization dewaxing is preferably 100 to 1,000 Nm$^3$/m$^3$, and more preferably 200 to 800 Nm$^3$/m$^3$. If the supply ratio is less than 100 Nm$^3$/m$^3$, for example, when the oil to be treated contains sulfur or nitrogen content, hydrogen sulfide and ammonia gas produced by desulfurization and denitrification reactions that accompany the isomerization reaction are adsorbed onto and poison the active metal on the catalyst, which tends to make it difficult to achieve a predetermined catalytic performance. Conversely, if the supply ratio is more than 1,000 Nm$^3$/m$^3$, hydrogen supply equipment having an increased capacity is required, which tends to make it difficult to realize an economical process.

It is preferred that the dewaxed oil obtained by the second step has a normal paraffin concentration of 10% by volume or less, and more preferably 1% by volume or less.

The method for producing a lubricating base oil according to the present embodiment may include a step of obtaining a hydrorefined oil by hydrorefining the dewaxed oil obtained through such a second step (hereinafter, referred to as "hydrorefining step" in some cases) and a step of obtaining a lubricating base oil by fractionating the hydrorefined oil (hereinafter, referred to as "product distillation step" in some cases) after the above-described second step.

(Hydrorefining Step)

In the hydrorefining step, a hydrorefined oil is obtained by hydrorefining the dewaxed oil obtained in the second step. By hydrorefining, for example, the olefins and aromatic compounds in the dewaxed oil are hydrogenated, so that the oxidation stability and the color hue of the lubricant are improved. Further, sulfur compounds in the dewaxed oil are hydrogenated, so that a decrease in the sulfur content can also be expected.

The hydrorefining can be carried out by, in the presence of hydrogen, bringing the dewaxed oil into contact with a hydrorefining catalyst. Examples of the hydrorefining catalyst preferably used include catalysts that include a support including one or more inorganic solid acidic substances selected from alumina, silica, zirconia, titania, boria, magnesia, and phosphorus, and one or more active metals selected from the group consisting of platinum, palladium, nickel-molybdenum, nickel-tungsten, and nickel-cobalt-molybdenum that is supported on the support (hereinafter, referred to as a "hydrorefining catalyst D").

A preferred support of a hydrorefining catalyst D is an inorganic solid acidic substance that includes at least two of alumina, silica, zirconia, and titania.

As the method for supporting the active metals on the support, a conventional method such as impregnation or ion exchange may be employed.

The amount of the active metals supported in the hydrorefining catalyst D is preferably such that the total amount of metal is 0.1 to 25% by mass based on the support.

The average pore size of the hydrorefining catalyst D is preferably 6 to 60 nm, and more preferably 7 to 30 nm. If the average pore size is less than 6 nm, a sufficient catalytic activity tends not to be obtained, while if the average pore size is more than 60 nm, catalytic activity tends to decrease due to a decrease in the level of dispersion of the active metals.

It is preferred that the pore volume of the hydrorefining catalyst D is 0.2 mL/g or more. If the pore volume is less than 0.2 mL/g, degradation of the activity of the catalyst tends to occur earlier. Further, the pore volume of the hydrorefining catalyst may be 0.5 mL/g or less, for example. In addition, it is preferred that the specific surface area of the hydrorefining catalyst is 200 m$^2$/g or more. If the specific surface area of the catalyst is less than 200 m$^2$/g, the dispersibility of the active metals is insufficient, so that activity tends to decrease. Still further, the specific surface area of hydrorefining catalyst may be 400 m²/g or less, for example. The pore volume and the specific surface area of the catalyst can be measured and calculated by a BET method using nitrogen adsorption.

It is preferred that reaction conditions of the hydrorefining catalyst D are set to, for example, a reaction temperature of 200 to 300° C., a hydrogen partial pressure of 3 to 20 MPa, an LHSV of 0.5 to 5 h$^{-1}$, and a hydrogen/oil ratio of 170 to 850 Nm³/m³, and more preferred are a reaction temperature of 200 to 300° C., a hydrogen partial pressure of 4 to 18 MPa, an LHSV of 0.5 to 4 h$^{-1}$, and a hydrogen/oil ratio of 340 to 850 Nm³/m³.

In the present embodiment, it is preferred to adjust the reaction conditions so that the sulfur and nitrogen content in the hydrorefined oil is 5 ppm by mass or less and 1 ppm by mass or less, respectively. The sulfur content is a value measured based on JIS K2541 "Crude oil and petroleum products—Determination of sulfur content," and the nitrogen content is a value measured based on HS K2609 "Crude petroleum and petroleum products—Determination of nitrogen content."

(Product Distillation Step)

In the second distillation step, the hydrorefined oil is fractionated to obtain a lubricating base oil.

The distillation conditions in the product distillation step are not especially limited, as long as the conditions allow the hydrorefined oil to be fractionated into the lubricant fraction. For example, it is preferred that the product distillation step is carried out by atmospheric distillation (or distillation under pressure) for distilling away the light fractions from the hydrorefined oil, and vacuum distillation for fractionating lubricant fraction from the bottom oil of the atmospheric distillation.

In the product distillation step, for example, a plurality of lubricant fractions are obtained by setting a plurality of cut points and performing vacuum distillation of a bottom oil obtained by atmospheric distillation (or distillation under pressure) of the hydrorefined oil. In the product distillation step, for example, a first lubricant fraction that has a boiling point range of 330 to 410° C. at atmospheric pressure, and a second lubricant fraction that has a boiling point range of 410 to 460° C. at atmospheric pressure can each be fractionated and collected from the hydrorefined oil.

The first lubricant fraction can be acquired as a lubricating base oil that is suited for ATF and shock absorbers. In this case, it is preferred that the kinematic viscosity of target value at 100° C. is 2.7 mm²/s. The second lubricant fraction can be acquired as the lubricating base oil according to the present invention that is suited as an engine oil base oil satisfying the API Group III and III+ standards. In this case, it is preferred that the kinematic viscosity of target value at 100° C. is 4.0 mm²/s, and that the pour point is −20° C. or less. The first lubricant fraction can be acquired as a lubricating base oil corresponding to 70 Pale, and the second lubricant fraction can be acquired as a lubricating base oil corresponding to SAE-10.

In addition, light fractions, such as naphtha or kerosene and gas oil, produced as a byproduct along with the hydrorefining is included in the hydrorefined oil obtained in the hydrorefining step. In the product distillation step, these light fractions can be collected as a fraction having a boiling point of 330° C. or less, for example.

In the present embodiment, the lubricating base oil can also be obtained by a product distillation step of obtaining a lubricant fraction by fractionating the dewaxed oil obtained in the second step, and a hydrorefining step of hydrorefining the lubricant fraction. In this case, the product distillation step and the hydrorefining step can be carried out in the same manner as the above-described product distillation step and hydrorefining step.

Next, a preferred embodiment of the present invention will be described more specifically with reference to the drawing.

Figure 2:
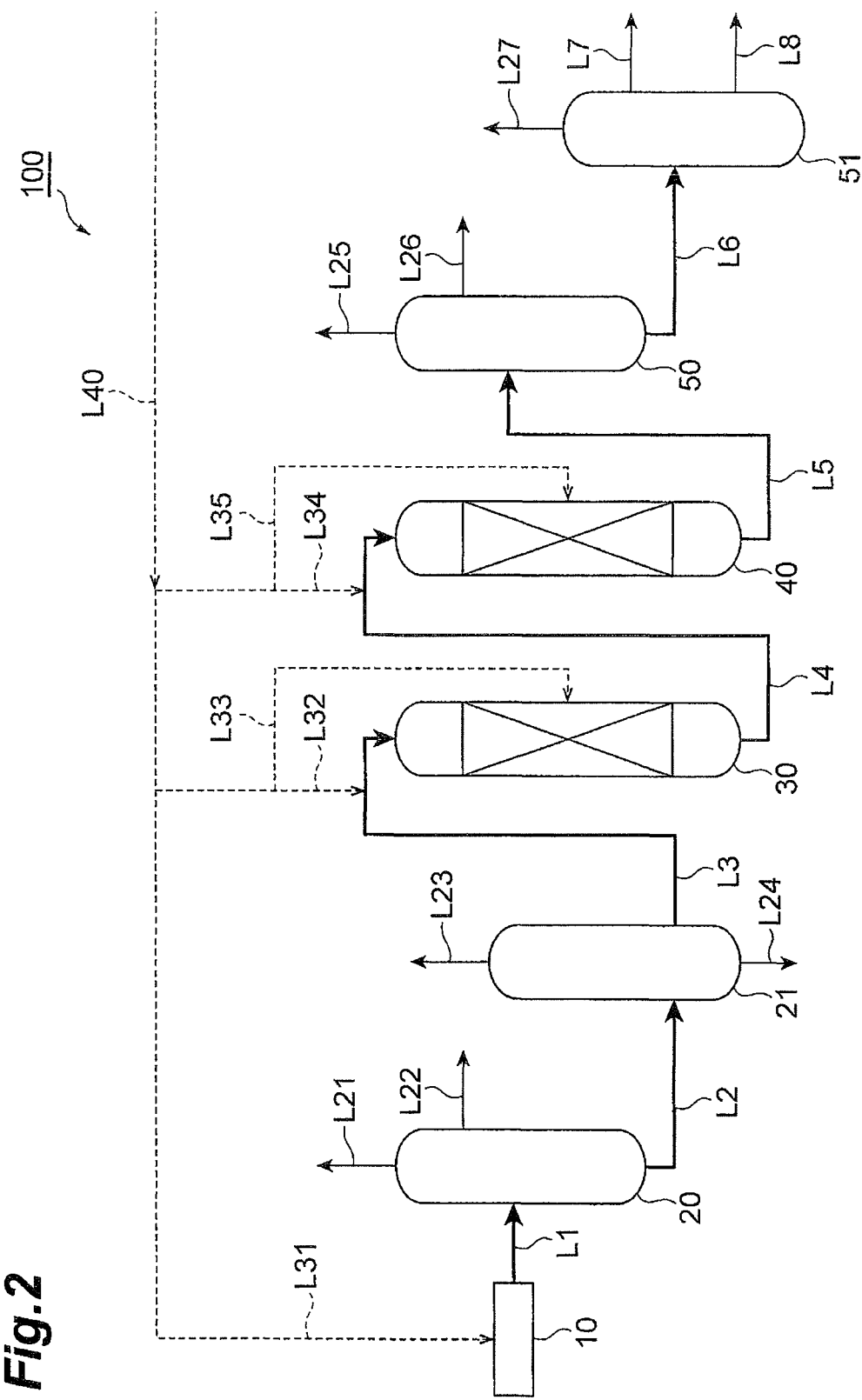
FIG. 2 is a flow diagram illustrating an example of a lubricating base oil production apparatus used in the method for producing a lubricating base oil according to the embodiment of the present invention.

FIG. 2 is a flow diagram illustrating an example of a lubricating base oil production apparatus used in the method for producing a lubricating base oil according to the embodiment of the present invention.

A lubricating base oil production apparatus 100 illustrated in FIG. 2 includes a pre-treatment reactor 10 for performing pre-treatment of a hydrocarbon oil, a raw material atmospheric distillation tower 20 for separating a light fraction from the pre-treated hydrocarbon oil that is supplied from the pre-treatment reactor 10 via a flow channel L1, a raw material vacuum distillation tower 21 for fractionating an oil fraction to be treated from the bottom oil that is supplied from the raw material atmospheric distillation tower 20 via a flow channel L2, an isomerization dewaxing reactor 30 for isomerization dewaxing of the oil to be treated that is supplied from the raw material vacuum distillation tower 21 via a flow channel L3, a hydrorefining reactor 40 for hydrorefining the dewaxed oil that is supplied from the isomerization dewaxing reactor 30 via a flow channel L4, a product atmospheric distillation tower 50 for separating a light fraction from the hydrorefined oil that is supplied from the hydrorefining reactor 40 via a flow channel L5, and a product vacuum distillation tower 51 for fractionating a lubricating base oil fraction from the bottom oil that is supplied from the product atmospheric distillation tower 50 via a flow channel L6.

A flow channel L21 for extracting a light gas component out of the system and a flow channel L22 for extracting light fractions such as naphtha, and kerosene and gas oil, out of the system from the pre-treated hydrocarbon oil are provided in the raw material atmospheric distillation tower 20.

A flow channel L23 for extracting a light fraction that is lighter than the oil fraction to be treated out of the system, and a flow channel L24 for extracting a heavy fraction that is heavier than the oil fraction to be treated out of the system are provided in the raw material vacuum distillation tower 21.

A flow channel L25 for extracting a light gas component out of the system and a flow channel L26 for extracting light fractions such as naphtha, and kerosene and gas oil, out of the system from the hydrorefined oil are provided in the product atmospheric distillation tower 50.

A flow channel L7 and a flow channel L8 for extracting a lubricant fraction that is fractionated in accordance with desirable lubricating base oil out of the system, and a flow channel L27 for extracting a fraction that is lighter than the lubricant fraction out of the system are provided in the product vacuum distillation tower 51.

Hydrogen gas is supplied to the pre-treatment reactor 10, the isomerization dewaxing reactor 30, and the hydrorefining reactor 40 via a flow channel L40.

A flow channel L31 that is branched from the flow channel L40 and connected to the pre-treatment reactor 10 is provided in the lubricating base oil production apparatus 100, and hydrogen gas supplied from the flow channel L31 is used for the pre-treatment step such as hydrocracking treatment and hydroisomerization treatment.

A flow channel L32 that is branched from the flow channel L40 and connected to the flow channel L3 is also provided in the lubricating base oil production apparatus 100, and hydrogen gas supplied from the flow channel L32 is mixed with the oil fraction to be treated in the flow channel L3 to be introduced into the isomerization dewaxing reactor 30. Moreover, a flow channel L33 that is branched from the flow channel L32 is connected to the isomerization dewaxing reactor 30, and a hydrogen pressure and a catalyst layer temperature in the isomerization dewaxing reactor 30 are adjusted by supply of hydrogen gas from the flow channel L33.

A flow channel L34 that is branched from the flow channel L40 and connected to the flow channel L4 is further provided in the lubricating base oil production apparatus 100, and hydrogen gas supplied from the flow channel L34 is mixed with the dewaxed oil in the flow channel L4 to be introduced into the hydrorefining reactor 40. Moreover, a flow channel L35 that is branched from the flow channel L34 is connected to the hydrorefining reactor 40, and a hydrogen pressure and a catalyst layer temperature in the hydrorefining reactor 40 are adjusted by supply of hydrogen gas from the flow channel L35.

In the lubricating base oil production apparatus 100, the pre-treatment step is performed in the pre-treatment reactor 10. In the pre-treatment reactor 10, in the presence of hydrogen supplied from the flow channel L31, different treatment is performed according to the kind of the hydrocarbon oil. In the case where the hydrocarbon oil is subjected to the hydrocracking treatment, the hydrocracking treatment can be performed by bringing the hydrocarbon oil into contact with the hydrocracking catalyst A-1 or A-2. In the case where the hydrocarbon oil is subjected to the hydroisomerization treatment, the hydroisomerization treatment can be performed by bringing the hydrocarbon oil into contact with the hydroisomerization catalyst B.

In the lubricating base oil production apparatus 100, the raw material distillation step is performed in the raw material atmospheric distillation tower 20 and the raw material vacuum distillation tower 21. In the raw material atmospheric distillation tower 20, by performing atmospheric distillation of the pre-treated hydrocarbon oil supplied from the flow channel L1, the light fraction can be extracted from the flow channel L22 and the bottom oil containing the oil fraction to be treated can be extracted from the flow channel L2. Moreover, in the raw material vacuum distillation tower 21, by performing vacuum distillation of the bottom oil supplied from the flow channel L2, the oil fraction to be treated can be extracted from the flow channel L3 and the heavy fraction can be extracted from the flow channel L24.

In the raw material vacuum distillation tower 21 of FIG. 2, one fraction as the oil fraction to be treated is fractionated and extracted, but two or more fractions as the oil fraction to be treated can be fractionated and extracted. Moreover, the extracted oil fraction to be treated may be temporarily stored in a tank or the like before subjecting to the first step or after subjecting to the first step.

In the lubricating base oil production apparatus 100, the first step is performed with respect to the oil to be treated supplied from the raw material vacuum distillation tower 21 via the flow channel L3. The $^{13}$C-NMR analysis is performed with respect to the oil to be treated, and the oil to be treated can be selected based on the above-described index values (1), (2) and (3) in the obtained $^{13}$C-NMR spectrum.

In the lubricating base oil production apparatus 100, the second step is performed in the isomerization dewaxing reactor 30. In the isomerization dewaxing reactor 30, the oil to be treated is subjected to isomerization dewaxing by, in the presence of hydrogen supplied from the flow channel L32 and the flow channel L33, bringing the oil to be treated supplied from the flow channel L3 into contact with the isomerization dewaxing catalyst.

In the lubricating base oil production apparatus 100, the hydrorefining step is performed in the hydrorefining reactor 40. In the hydrorefining reactor 40, the dewaxed oil is hydrorefined by, in the presence of hydrogen supplied from the flow channel L34 and the flow channel L35, bringing the dewaxed oil supplied from the flow channel L4 into contact with the hydrorefining catalyst.

In the lubricating base oil production apparatus 100, the product distillation step is performed in the product atmospheric distillation tower 50 and the product vacuum distillation tower 51. In the product atmospheric distillation tower 50, by performing atmospheric distillation of the hydrorefined oil supplied from the flow channel L5, the light fraction can be extracted from the flow channel L26 and the bottom oil containing the lubricant fraction can be extracted from the flow channel L6. Moreover, in the product vacuum distillation tower 51, by performing vacuum distillation of the bottom oil supplied from the flow channel L6, the lubricant fractions can be extracted from the flow channel L7 and the flow channel L8, and the lubricant fractions can be suitably used as a lubricating base oil, respectively.

In the product vacuum distillation tower 51 of FIG. 2, two fractions as the lubricant fraction are fractionated and extracted, but a single fraction as the lubricant fraction may be extracted, and three or more fractions as the lubricant fraction can be fractionated and extracted. Moreover, a flow channel for extracting a fraction that is lighter than the lubricant fraction may be provided in the product vacuum distillation tower 51.

Although a preferred embodiment of the present invention was described above, the present invention is not limited to the above-described embodiment.

EXAMPLES

Although the present invention will now be described more specifically based on the following Examples, the present invention is not limited to the Examples.

Production Example 1

Preparation of Hydrocracking Catalyst A-1

A kneaded product was prepared by adding water into a mixture of 47% by mass of silica-alumina, 3% by mass of USY zeolite, and 50% by mass of alumina binder, and kneading the resultant mixture into a clay-like state. This kneaded product was extruded into a columnar shape having a diameter of about 1.5 mm and a length of about 3 mm by extrusion molding. The obtained extruded body was dried for 3 hours at 120° C., and then calcined in air for further 3 hours at 500° C. to obtain a support.

A chloroplatinic acid aqueous solution was impregnated into this support and supporting was carried out so that the amount of platinum was 0.8% by mass based on the mass of the support. Next, the obtained impregnated product (catalyst precursor) was dried for 3 hours at 120° C., and then calcined under an air flow for 1 hour at 500° C. to obtain a hydrocracking catalyst A-1.

Production Example 2

Preparation of Hydrocracking Catalyst A-2

A kneaded product was prepared by adding water into a mixture of 50% by mass of silica-zirconia and 50% by mass of alumina binder, and kneading the resultant mixture into a clay-like state. This kneaded product was extruded into a columnar shape having a diameter of about 1.5 mm and a length of about 3 mm by extrusion molding. The obtained extruded body was dried for 3 hours at 120° C., and then calcined in air for further 1 hour at 500° C. to obtain a support.

A supporting aqueous solution that was prepared with molybdenum trioxide, nickel carbonate, and phosphoric acid was impregnated into this support and supporting was carried out so that a nickel oxide was 5% by mass, a molybdenum oxide was 20% by mass, and a phosphorus oxide was 3% by mass based on the mass of the support. Next, the obtained impregnated product (catalyst precursor) was dried for 3 hours at 120° C., and then calcined under an air flow for 1 hour at 500° C. to obtain a hydrocracking catalyst A-2.

Production Example 3

Hydroisomerization Catalyst B

A kneaded product was prepared by adding water into a mixture of 60% by mass of silica-alumina and 40% by mass of alumina binder, and kneading the resultant mixture into a clay-like state. This kneaded product was extruded into a columnar shape having a diameter of about 1.6 mm and a length of about 4 mm by extrusion molding. The obtained extruded body was dried for 3 hours at 120° C., and then calcined in air for further 1 hour at 500° C. to obtain a support.

A chloroplatinic acid solution was impregnated into this support and supporting was carried out so that the amount of platinum was 0.8% by mass based on the mass of the support. Next, the obtained impregnated product (catalyst precursor) was dried for 3 hours at 120° C., and then calcined under an air flow for 3 hours at 400° C. to obtain a hydroisomerization catalyst B.

Production Example 4

Preparation of Isomerization dewaxing Catalyst C

<Production of Zeolite ZSM-22>

Zeolite ZSM-22 (hereinafter sometimes referred to as "ZSM-22") formed from crystalline aluminosilicate and having a Si/Al ratio of 45 was produced by hydrothermal synthesis based on the following procedure.

First, the following four types of aqueous solution were prepared.

Solution A: Solution in which 1.94 g of potassium hydroxide was dissolved in 6.75 mL of ion-exchanged water.

Solution B: Solution in which 1.33 g of aluminum sulfate 18-hydrate was dissolved in 5 mL of ion-exchanged water.

Solution C: Solution in which 4.18 g of 1,6-hexanediamine (organic template) was diluted with 32.5 mL of ion-exchanged water.

Solution D: Solution in which 18 g of colloidal silica (Ludox AS-40, manufactured by Grace Davison) was diluted with 31 mL of ion-exchanged water.

Next, solution A was added into solution B, and stirring was carried out until the aluminum component was completely dissolved. Solution C was added into the mixed solution, and then while vigorously stirring at room temperature, the mixture of solution A, B, and C was injected into solution D. In addition, as a "seed crystal" for promoting crystallization, 0.25 g of a separately-synthesized ZSM-22 powder that had not undergone any special treatments after being synthesized was added to the mixture to obtain a gel-like product.

The gel-like product obtained by the above operation was transferred into a stainless steel autoclave reactor with an internal volume of 120 mL, and hydrothermal synthesis reaction was carried out in a 150° C. oven for 60 hours by rotating the autoclave reactor on a tumbling apparatus at a rotational speed of about 60 rpm. After the reaction was finished, the reactor was cooled, and then opened. The product was dried overnight in a 60° C. dryer to obtain ZSM-22 having a Si/Al ratio of 45.

<Ion Exchange of ZSM-22 Containing an Organic Template>

An ion-exchange treatment was carried out on the thus-obtained ZSM-22 with an aqueous solution containing ammonium ions by the following operation.

The thus-obtained ZSM-22 was placed in a flask. 100 mL of 0.5 N aqueous ammonium chloride per 1 g of zeolite ZSM-22 was added, and the resultant mixture was heated under reflux for 6 hours. The mixture was cooled to room temperature, the supernatant was then removed, and the crystalline aluminosilicate was washed with ion-exchanged water. The same amount as above of 0.5 N aqueous ammonium chloride was again added, and the resultant mixture was heated under reflux for 12 hours.

Subsequently, the solid content was collected by filtration, washed with ion-exchanged water, and dried overnight in a 60° C. dryer to obtain ion-exchanged $NH_4$-type ZSM-22. This ZSM-22 was an ion-exchanged zeolite in a state that included an organic template.

<Binder Blending, Extruding, Calcining>

The above-obtained $NH_4$-type ZSM-22 and alumina as a binder were mixed in a mass ratio of 7:3, a small amount of ion-exchanged water was added, and the resultant mixture was kneaded. The obtained viscous fluid was loaded in an extrusion molder, and then extruded into a cylindrical extruded body having a diameter of about 1.6 mm and a length of about 10 mm. The extruded body was heated under a nitrogen atmosphere for 3 hours at 300° C. to obtain a support precursor.

<Platinum Supporting and Calcining>

An impregnation solution was obtained by dissolving tetraammineplatinum dinitrate $[Pt(NH_3)_4](NO_3)_2$ in ion-exchanged water equivalent to an amount of the water absorption of the support precursor measured in advance. This solution was impregnated into the above-described support precursor by an incipient wetness method and supporting was carried out so that the amount of platinum was 0.3% by mass based on the mass of the zeolite ZSM-22. Next, the obtained impregnated product (catalyst precursor) was dried overnight in a 60° C. dryer, and then calcined under an air flow for 3 hours at 400° C. to obtain an isomerization dewaxing catalyst C in which the amount of carbon is 0.56% by mass. The amount of carbon of the isomerization dewaxing catalyst C was analyzed by a combustion in oxygen flow-infrared absorption method (measurement apparatus: HORIBA, Ltd. EMIA-920V). Specifically, the catalyst C was burned in the oxygen flow and quantitation of the amount of carbon was performed by the infrared absorption method.

In addition, the micropore volume per unit mass of the obtained isomerization dewaxing catalyst C was calculated by the following method. First, to remove moisture adsorbed to the isomerization dewaxing catalyst C, a pre-treatment was carried out for evacuating for 5 hours at 150° C. A nitrogen adsorption measurement was carried out on the pre-treated isomerization dewaxing catalyst C at the temperature of liquid nitrogen (−196° C.) using a BELSORP-max, manufactured by BEL Japan, Inc. Then, the micropore volume (cm$^3$/g) per unit mass of the isomerization dewaxing catalyst C was calculated by analyzing the adsorption isotherm of the measured nitrogen by a t-plot method.

Further, the micropore volume $V_z$ per unit mass of the zeolite contained in the catalyst was calculated based on the following expression. When the nitrogen adsorption measurement for the alumina used as a binder was carried out in the same manner as described above, it was confirmed that the alumina did not have any micropores.

$$V_z = V_c/M_z \times 100$$

In the expression, $V_c$ represents the micropore volume per unit mass of the isomerization dewaxing catalyst C, and $M_z$ represents the content (% by mass) of zeolite contained in the catalyst.

The micropore volume per unit mass of the isomerization dewaxing catalyst C was 0.055 cm$^3$/g, and the micropore volume per unit mass of the zeolite contained in the catalyst was 0.079 cm$^3$/g.

Production Example 5

Hydrorefining Catalyst D

A kneaded product was prepared by adding water into a mixture of 50% by mass of silica-zirconia and 50% by mass of alumina binder, and kneading the resultant mixture into a clay-like state. This kneaded product was extruded into a columnar shape having a diameter of about 1.5 mm and a length of about 3 mm by extrusion molding. The obtained extruded body was dried for 3 hours at 120° C., and then calcined in air for further 3 hours at 500° C. to obtain a support.

A chloroplatinic acid solution was impregnated into this support and supporting was carried out so that the amount of platinum was 0.3% by mass and palladium was 0.3% by mass based on the mass of the support. Next, the obtained impregnated product (catalyst precursor) was dried for 3 hours at 120° C., and then calcined under an air flow for 1 hour at 500° C. to obtain a hydrorefining catalyst D.

Example 1(a)

A heavy FT synthetic oil (boiling point range of 520 to 600° C.) was subjected to hydrocracking at a hydrocracking reaction temperature of 308° C., a hydrogen partial pressure of 4 MPa, a hydrogen/oil ratio of 4000 scf/bbl (674 Nm$^3$/m$^3$), and a liquid hourly space velocity of 2 h$^{-1}$. As a hydrocracking catalyst, the hydrocracking catalyst A-1 was used.

The obtained pre-treated hydrocarbon oil was fractionated into a light gas component, a fraction having a boiling point of 330° C. or less (light fraction), and a fraction having a boiling point of more than 330° C. (pre-treated hydrocarbon oil fraction) in the atmospheric distillation tower. The pre-treated hydrocarbon oil was fractionated into a fraction having a boiling point of 460° C. or less (oil fraction to be treated) and a fraction having a boiling point of more than 460° C. (heavy fraction) by vacuum distillation. In the obtained oil fraction to be treated, the distillation 10% by volume distillation temperature (T10) was 344° C., the distillation 50% by volume distillation temperature (T50) was 398° C., the distillation 90% by volume distillation temperature (T90) was 454° C., the acyclic saturated component (chain saturated hydrocarbon component) was 100% by mass, the isomer ratio (isoparaffin component/paraffin component) was 90% by mass, the average carbon number was 28, the index value (1) was 0.08, the index value (2) was 0.25, and the index value (3) was 0.17.

The oil fraction to be treated was subjected to isomerization dewaxing at an isomerization dewaxing reaction temperature of 315° C., a hydrogen partial pressure of 5 MPa, a hydrogen/oil ratio of 3000 scf/bbl (505.5 Nm$^3$/m$^3$), and a liquid hourly space velocity of 1 h$^{-1}$. As an isomerization dewaxing catalyst, the isomerization dewaxing catalyst C was used. The oil fraction to be treated which was subjected to the isomerization dewaxing (dewaxed oil) was subjected to hydrorefining, using the hydrorefining catalyst D, at a hydrorefining reaction temperature of 190° C., a hydrogen partial pressure of 5 MPa, a hydrogen/oil ratio of 3000 scf/bbl (505.5 Nm$^3$/m$^3$), and a liquid hourly space velocity of 1.5 h$^{-1}$, and fractionated in the atmospheric distillation tower and the vacuum distillation tower to obtain a lubricating base oil 1 (70 Pale: fraction having boiling point range of 330 to 410° C.) and a lubricating base oil 2 (SAE-10: fraction having boiling point range of 410 to 460° C.). The result is shown in Table 1.

In Table 1 and Table 2, in distillation characteristics of a hydrogenation pre-treated generated oil (pre-treated hydrocarbon oil) measured based on JIS K2254 "Petroleum products-Determination of distillation characteristics-Gas chromatographic method", the cracking ratio in hydrogenation pre-treatment indicates a ratio of hydrocarbon, expressed in volume percentage, which is lighter, namely, has a lower boiling point than 90% by volume distillation temperature of distillation characteristics of a hydrogenation pre-treated feedstock. In the oil to be treated characteristics, the distillation characteristics (T10, T50, T90) are values measured based on the above-described JIS K2254 "Petroleum products-Determination of distillation characteristics-Gas chromatographic method". The acyclic saturated component is a value determined by a gas chromatography analysis. The isomer ratio is a value calculated based on an isoparaffin component and a paraffin component (isoparaffin component/paraffin component), which are determined by a gas chromatography analysis. The average carbon number is a value determined by performing a gas chromatography analysis and from, with reference to gas chromatogram of a normal paraffin mixture, which is measured under the same conditions, the sum of a product of the component ratio of each carbon number and the carbon number based on a measurement result of the carbon number distribution and the component ratio of each carbon number of the lubricating base oil. Regarding the gas chromatography analysis, the measurement was performed under the following conditions, by using GC-2010 manufactured by Shimadzu Corporation.

Column: UltraALLOY-1HT (30 m×0.25 mmφ), Carrier Gas: He 200 kPa, Detector: FID, Detector Temperature: 350° C., Column Oven Temperature: 50° C. to 320° C., Column Temperature Increase Rate: 6° C./min, Injector Volume: 0.4 μL (split ratio 70/1).

As described above, the index values (1), (2) and (3) were determined based on a $^{13}$C-NMR spectrum obtained by a $^1$H-gated decoupling method and a DEPT135 method, by using AVANCE400 (9.4 T) manufactured by Bruker Corporation for a $^{13}$C-NMR analysis of an oil to be treated. The measurement was performed using a sample in which the oil to be treated is dissolved in deuterated chloroform (the concentration of the oil to be treated is 15 to 25% by volume)

at a 30° pulse, wait time of 10 seconds, a temperature of 60° C., and the cumulative number of 2560 times.

index value (1): a value obtained by dividing an integrated value of a peak assigned to a tertiary carbon atom by an integrated value of all peaks at 0 to 50 ppm, index value (2): a value obtained by dividing an integrated value of a peak assigned to a carbon atom constituting a hydrocarbon main chain by the integrated value of all peaks at 0 to 50 ppm, and index value (3): a value obtained by dividing an integrated value of a peak assigned to a branched $CH_3$ bonded to a fifth carbon atom or a carbon atom on an inner side thereof from a terminal carbon atom in the hydrocarbon main chain by an integrated value of all peaks at 10 to 25 ppm.

The index values (4) and (5) are values determined as follows.

index value (4): an average carbon number determined from the above-described gas chromatography analysis, and index value (5): a product of the index value (2) and the index value (4).

Moreover, in the lubricating base oil 1 (70 Pale), the lubricating base oil 2 (SAE-10), and the lubricating base oil 3 (SAE-20) in Table 1 and Table 2, the 100° C. kinematic viscosity ($mm^2/s$) is kinematic viscosity at 100° C., which is measured based on JIS K2283 "Crude petroleum and petroleum products-Determination of kinematic viscosity and calculation of viscosity index from kinematic viscosity-Determination of kinematic viscosity", the pour point is a pour point measured based on JIS K2269 "Testing Methods for Pour Point and Cloud Point of Crude Oil and Petroleum Products-Testing Method for Pour Point", and the viscosity index is a value calculated based on JIS K2283 "Crude petroleum and petroleum products-Determination of kinematic viscosity and calculation of viscosity index from kinematic viscosity-Calculation of viscosity index from kinematic viscosity".

Example 1(b)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 1(a) except that the isomerization dewaxing reaction temperature was changed to 325° C. The result is shown in Table 1.

Example 2(a)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 1(a) except that an oil fraction to be treated having the index value (1) of 0.06, the index value (2) of 0.35, and the index value (3) of 0.13 was used and the isomerization dewaxing reaction temperature was changed to 320° C. The result is shown in Table 1.

Example 2(b)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 2(a) except that the isomerization dewaxing reaction temperature was changed to 305° C. The result is shown in Table 1.

Example 3

A lubricating base oil 3 (SAE-20: fraction having boiling point range of 460 to 520° C.) was obtained in the same manner as Example 1(a) except that an oil fraction to be treated having the average carbon number of 33, the index value (1) of 0.07, the index value (2) of 0.31, and the index value (3) of 0.15 was used and the isomerization dewaxing reaction temperature was changed to 322° C. The result is shown in Table 1.

Example 4

A light FT synthetic oil (boiling point range of 330 to 520° C.) was subjected to hydroisomerization at a reaction temperature of 315° C., a hydrogen partial pressure of 3 MPa, a hydrogen/oil ratio of 3000 scf/bbl (506 $Nm^3/m^3$), and a liquid hourly space velocity of 2 $h^{-1}$. As a hydroisomerization catalyst, the hydroisomerization catalyst B was used.

The obtained pre-treated hydrocarbon oil was fractionated into a fraction having a boiling point of 330° C. or less (light fraction), and a fraction having a boiling point of more than 330° C. (pre-treated hydrocarbon oil fraction) by atmospheric distillation. The pre-treated hydrocarbon oil was fractionated into a fraction having a boiling point of 460° C. or less (oil fraction to be treated) and a fraction having a boiling point of more than 460° C. (heavy fraction) by vacuum distillation. In the obtained oil fraction to be treated, the distillation 10% by volume distillation temperature (T10) was 347° C., the distillation 50% by volume distillation temperature (T50) was 400° C., the distillation 90% by volume distillation temperature (T90) was 458° C., the acyclic saturated component (chain saturated hydrocarbon component) was 100% by mass, the isomer ratio was 40% by mass, the average carbon number was 28, the index value (1) was 0.02, the index value (2) was 0.55, and the index value (3) was 0.08.

The oil fraction to be treated was subjected to isomerization dewaxing at an isomerization reaction temperature of 330° C., a hydrogen partial pressure of 5 MPa, a hydrogen/oil ratio of 3000 scf/bbl (505.5 $Nm^3/m^3$), and a liquid hourly space velocity of 1 $h^{-1}$. As an isomerization dewaxing catalyst, the isomerization dewaxing catalyst C was used. The oil fraction to be treated which was subjected to the isomerization dewaxing (dewaxed oil) was subjected to hydrorefining, using the hydrorefining catalyst D, at a hydrorefining reaction temperature of 190° C., a hydrogen partial pressure of 5 MPa, a hydrogen/oil ratio of 3000 scf/bbl (505.5 $Nm^3/m^3$), and a liquid hourly space velocity of 1.5 $h^{-1}$, and fractionated in the atmospheric distillation tower and the vacuum distillation tower to obtain a lubricating base oil 1 (70 Pale: fraction having boiling point range of 330 to 410° C.) and a lubricating base oil 2 (SAE-10: fraction having boiling point range of 410 to 460° C.). The result is shown in Table 1.

Example 5

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 4 except that an oil fraction to be treated having the index value (1) of 0.01, the index value (2) of 0.6, and the index value (3) of 0.05 was used and the isomerization dewaxing reaction temperature was changed to 338° C. The result is shown in Table 1.

35

Example 6

A lubricating base oil 3 (SAE-20: fraction having boiling point range of 460 to 520° C.) was obtained in the same manner as Example 4 except that an oil fraction to be treated having the average carbon number of 33, the index value (1) of 0.02, the index value (2) of 0.55, and the index value (3) of 0.08 was used and the isomerization dewaxing reaction temperature was changed to 333° C. The result is shown in Table 1.

Example 7

A heavy slack wax (boiling point range of 520 to 680° C.) was subjected to hydrocracking at a reaction temperature of 375° C., a hydrogen partial pressure of 5.8 MPa, a hydrogen/oil ratio of 3000 scf/bbl (506 Nm$^3$/m$^3$), and a liquid hourly space velocity of 2 h$^{-1}$. As a hydrocracking catalyst, the hydrocracking catalyst A-2 was used.

The obtained pre-treated hydrocarbon oil was fractionated into a light gas component, a fraction having a boiling point of 330° C. or less (light fraction), and a fraction having a boiling point of more than 330° C. (pre-treated hydrocarbon oil fraction) by atmospheric distillation. The pre-treated hydrocarbon oil was fractionated into a fraction having a boiling point of 460° C. or less (oil fraction to be treated) and a fraction having a boiling point of more than 460° C. or more (heavy fraction) by vacuum distillation. In the obtained oil fraction to be treated, the distillation 10% by volume distillation temperature (T10) was 350° C., the distillation 50% by volume distillation temperature (T50) was 403° C., the distillation 90% by volume distillation temperature (T90) was 458° C., the acyclic saturated component (chain saturated hydrocarbon component) was 80% by mass, the isomer ratio was 90% by mass, the average carbon number was 28, the index value (1) was 0.07, the index value (2) was 0.3, and the index value (3) was 0.15.

The oil fraction to be treated was subjected to isomerization dewaxing at an isomerization reaction temperature of 320° C., a hydrogen partial pressure of 5 MPa, a hydrogen/oil ratio of 3000 scf/bbl (505.5 Nm$^3$/m$^3$), and a liquid hourly space velocity of 1 h$^{-1}$. As an isomerization dewaxing catalyst, the isomerization dewaxing catalyst C was used. The oil fraction to be treated which was subjected to the isomerization dewaxing (dewaxed oil) was subjected to hydrorefining, using the hydrorefining catalyst D, at a hydrorefining reaction temperature of 225° C., a hydrogen partial pressure of 5 MPa, a hydrogen/oil ratio of 3000 scf/bbl (505.5 Nm$^3$/m$^3$), and a liquid hourly space velocity of 1.5 h$^{-1}$, and fractionated in the atmospheric distillation tower and the vacuum distillation tower to obtain a lubricating base oil 1 (70 Pale: fraction having boiling point range of 330 to 410° C.) and a lubricating base oil 2 (SAE-10: fraction having boiling point range of 410 to 460° C.). The result is shown in Table 1.

Example 8

A lubricating base oil 0.1 (70 Pale: fraction having boiling point range of 330 to 410° C.) and a lubricating base oil 2 (SAE-10: fraction having boiling point range of 410 to 460° C.) were obtained in the same manner as Example 7 except that a slack wax (boiling point range of 390 to 460° C.) having the index value (1) of 0.03, the index value (2) of 0.5, and the index value (3) of 0.1 was used as an oil to be treated. The result is shown in Table 1.

36

Comparative Example 1(a)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 1(a) except that an oil fraction to be treated having the index value (1) of 0.15, the index value (2) of 0.15, and the index value (3) of 0.25 was used and the isomerization dewaxing reaction temperature was changed to 320° C. The result is shown in Table 2.

Comparative Example 1(b)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Comparative Example 1(a) except that the isomerization dewaxing reaction temperature was changed to 310° C. The result is shown in Table 2.

Comparative Example 2(a)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 1(a) except that a light FT synthetic oil (boiling point range of 330 to 520° C.) having the index value (1) of 0.003, the index value (2) of 0.7, and the index value (3) of 0.02 was used as an oil to be treated and the isomerization dewaxing reaction temperature was changed to 320° C. The result is shown in Table 2.

Comparative Example 2(b)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Comparative Example 2(a) except that the isomerization dewaxing reaction temperature was changed to 340° C. The result is shown in Table 2.

Comparative Example 3(a)

A lubricating base oil 3 (SAE-20: fraction having boiling point range of 460 to 520° C.) was obtained in the same manner as Example 1(a) except that an oil fraction to be treated having the average carbon number of 33, the index value (1) of 0.16, the index value (2) of 0.14, and the index value (3) of 0.26 was used and the isomerization dewaxing reaction temperature was changed to 322° C. The result is shown in Table 2.

Comparative Example 3(b)

A lubricating base oil 3 (SAE-20: fraction having boiling point range of 460 to 520° C.) was obtained in the same manner as Comparative Example 3(a) except that the isomerization dewaxing reaction temperature was changed to 311° C. The result is shown in Table 2.

Comparative Example 4(a)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Example 7 except that an oil fraction to be treated having the index value (1)

of 0.13, the index value (2) of 0.13, and the index value (3) of 0.22 was used. The result is shown in Table 2.

Comparative Example 4(b)

A lubricating base oil 1 (70 Pale: fraction having boiling point range of 330 to 410° C.) and a lubricating base oil 2 (SAE-10: fraction having boiling point range of 410 to 460° C.) were obtained in the same manner as Comparative Example 4(a) except that the isomerization dewaxing reaction temperature was changed to 310° C. The result is shown in Table 2.

TABLE 1

| | | Example 1(a) | Example 1(b) | Example 2(a) | Example 2(b) | Example 3 |
|---|---|---|---|---|---|---|
| Hydrogenation Pre-Treatment | Hydrocarbon Oil | Heavy FT Synthetic Oil | Heavy FT Synthetic Oil | Heavy FT Synthetic Oil | Heavy FT Synthetic Oil | Heavy FT Synthetic Oil |
| | Pre-Treatment Catalyst | Hydrocracking Hydrocracking Catalyst A-1 | Hydrocracking Hydrocracking Catalyst A-1 | Hydrocracking Hydrocracking Catalyst A-1 | Hydrocracking Hydrocracking Catalyst A-1 | Hydrocracking Hydrocracking Catalyst A-1 |
| | Temperature, ° C. | 308 | 300 | 300 | 300 | 305 |
| | Hydrogen Partial Pressure, MPa | 4 | 4 | 4 | 4 | 4 |
| | LHSV, h$^{-1}$ | 2 | 2 | 2 | 2 | 2 |
| | Hydrogen/Oil Ratio, scf/bbl | 4000 | 4000 | 4000 | 4000 | 4000 |
| | Cracking Ratio, % | 48 | 26 | 26 | 26 | 38 |
| Oil to be Treated Characteristics | T10, ° C. | 344 | 345 | 345 | 345 | 463 |
| | T50, ° C. | 398 | 399 | 399 | 399 | 504 |
| | T90, ° C. | 454 | 455 | 455 | 455 | 527 |
| | Acyclic Saturated Component, % | 100 | 100 | 100 | 100 | 100 |
| | Isomer Ratio, % | 90 | 78 | 78 | 78 | 85 |
| | Average Carbon Number | 28 | 28 | 28 | 28 | 33 |
| | Index Value (1) | 0.08 | 0.06 | 0.06 | 0.06 | 0.07 |
| | Index Value (2) | 0.25 | 0.35 | 0.35 | 0.35 | 0.31 |
| | Index Value (3) | 0.17 | 0.13 | 0.13 | 0.13 | 0.15 |
| | Index Value (4) | 28 | 28 | 28 | 28 | 33 |
| | Index Value (5) | 7 | 9.8 | 9.8 | 9.8 | 10.2 |
| Isomerization Dewaxing | Catalyst | Isomerization Dewaxing Catalyst C | Isomerization Dewaxing Catalyst C | Isomerization Dewaxing Catalyst C | Isomerization Dewaxing Catalyst C | Isomerization Dewaxing Catalyst C |
| | Temperature, ° C. | 315 | 325 | 320 | 305 | 322 |
| | Hydrogen Partial Pressure, MPa | 5 | 5 | 5 | 5 | 5 |
| | LHSV, h$^{-1}$ | 1 | 1 | 1 | 1 | 1 |
| | Hydrogen/Oil Ratio, scf/bbl | 3000 | 3000 | 3000 | 3000 | 3000 |
| Hydrorefining | Catalyst | Hydrorefining Catalyst D | Hydrorefining Catalyst D | Hydrorefining Catalyst D | Hydrorefining Catalyst D | Hydrorefining Catalyst D |
| | Temperature, ° C. | 190 | 190 | 190 | 190 | 190 |
| | Hydrogen Partial Pressure, MPa | 5 | 5 | 5 | 5 | 5 |
| | LHSV, h$^{-1}$ | 1.5 | 1.5 | 1.5 | 1.5 | 1.5 |
| | Hydrogen/Oil Ratio, scf/bbl | 3000 | 3000 | 3000 | 3000 | 3000 |
| | Base Oil Yield, % (Oil to be Treated) | 68 | 65 | 66 | 70 | 66 |
| Lubricant Base Oil 1 (70Pale Characteristics) | 100° C. Kinematic Viscosity, mm$^2$/s | 2.7 | 2.7 | 2.7 | 2.7 | — |
| | Pour Point, ° C. | −35 | −45 | −35 | −35 | — |
| | Viscosity Index | 130 | 125 | 131 | 132 | — |
| Lubricant Base Oil 2 (SAE-10 Characteristics) | 100° C. Kinematic Viscosity, mm$^2$/s | 3.9 | 3.9 | 3.9 | 3.9 | — |
| | Pour Point, ° C. | −25 | −35 | −25 | −10 | — |
| | Viscosity Index | 143 | 140 | 143 | 150 | — |
| Lubricant Base Oil 3 (SAE-20 Characteristics) | 100° C. Kinematic Viscosity, mm$^2$/s | — | — | — | — | 6.2 |
| | Pour Point, ° C. | — | — | — | — | −15 |
| | Viscosity Index | — | — | — | — | 158 |

| | | Example 4 | Example 5 | Example 6 | Example 7 | Example 8 |
|---|---|---|---|---|---|---|
| Hydrogenation Pre-Treatment | Hydrocarbon Oil | Light FT Synthetic Oil | Light FT Synthetic Oil | Light FT Synthetic Oil | Heavy Slack Wax | Slack Wax |
| | Pre-Treatment Catalyst | Hydro isomerization Hydro isomerization Catalyst B | Hydro isomerization Hydro isomerization Catalyst B | Hydro isomerization Hydro isomerization Catalyst B | Hydrocracking Hydrocracking Catalyst A-2 | None — |

TABLE 1-continued

|  |  |  |  |  |  |  |
|---|---|---:|---:|---:|---:|---:|
|  | Temperature, °C. | 315 | 310 | 313 | 375 | — |
|  | Hydrogen Partial Pressure, MPa | 3 | 3 | 3 | 5.8 | — |
|  | LHSV, h$^{-1}$ | 2 | 2 | 2 | 1 | — |
|  | Hydrogen/Oil Ratio, scf/bbl | 3000 | 3000 | 3000 | 3000 | — |
|  | Cracking Ratio, % | 10 | 5 | 8 | 40 | — |
| Oil to be Treated Characteristics | T10, °C. | 347 | 346 | 464 | 350 | 350 |
|  | T50, °C. | 400 | 399 | 505 | 403 | 405 |
|  | T90, °C. | 458 | 457 | 528 | 458 | 457 |
|  | Acyclic Saturated Component, % | 100 | 100 | 100 | 80 | 90 |
|  | Isomer Ratio, % | 40 | 20 | 40 | 90 | 40 |
|  | Average Carbon Number | 28 | 28 | 33 | 28 | 28 |
|  | Index Value (1) | 0.02 | 0.01 | 0.02 | 0.07 | 0.03 |
|  | Index Value (2) | 0.55 | 0.6 | 0.55 | 0.3 | 0.5 |
|  | Index Value (3) | 0.08 | 0.05 | 0.08 | 0.15 | 0.1 |
|  | Index Value (4) | 28 | 28 | 33 | 28 | 28 |
|  | Index Value (5) | 15.4 | 16.8 | 18.2 | 8.4 | 14 |
| Isomerization Dewaxing | Catalyst | Isomerization Dewaxing Catalyst C | Isomerization Dewaxing Catalyst C | Isomerization Dewaxing Catalyst C | Isomerization Dewaxing Catalyst C | Isomerization Dewaxing Catalyst C |
|  | Temperature, °C. | 330 | 338 | 333 | 320 | 320 |
|  | Hydrogen Partial Pressure, MPa | 5 | 5 | 5 | 5 | 5 |
|  | LHSV, h$^{-1}$ | 1 | 1 | 1 | 1 | 1 |
|  | Hydrogen/Oil Ratio, scf/bbl | 3000 | 3000 | 3000 | 3000 | 3000 |
| Hydrorefining | Catalyst | Hydrorefining Catalyst D | Hydrorefining Catalyst D | Hydrorefining Catalyst D | Hydrorefining Catalyst D | Hydrorefining Catalyst D |
|  | Temperature, °C. | 190 | 190 | 190 | 225 | 225 |
|  | Hydrogen Partial Pressure, MPa | 5 | 5 | 5 | 5 | 5 |
|  | LHSV, h$^{-1}$ | 1.5 | 1.5 | 1.5 | 1.5 | 1.5 |
|  | Hydrogen/Oil Ratio, scf/bbl | 3000 | 3000 | 3000 | 3000 | 3000 |
|  | Base Oil Yield, % (Oil to be Treated) | 69 | 70 | 68 | 65 | 70 |
| Lubricant Base Oil 1 (70Pale Characteristics) | 100° C. Kinematic Viscosity, mm$^2$/s | 2.7 | 2.7 | — | 2.7 | 2.7 |
|  | Pour Point, °C. | −35 | −35 | — | −30 | −30 |
|  | Viscosity Index | 133 | 134 | — | 121 | 123 |
| Lubricant Base Oil 2 (SAE-10 Characteristics) | 100° C. Kinematic Viscosity, mm$^2$/s | 3.9 | 3.9 | — | 3.9 | 3.9 |
|  | Pour Point, °C. | −25 | −25 | — | −25 | −25 |
|  | Viscosity Index | 145 | 146 | — | 140 | 142 |
| Lubricant Base Oil 3 (SAE-20 Characteristics) | 100° C. Kinematic Viscosity, mm$^2$/s | — | — | 6.1 | — | — |
|  | Pour Point, °C. | — | — | −15 | — | — |
|  | Viscosity Index | — | — | 160 | — | — |

TABLE 2

|  |  | Comparative Example 1(a) | Comparative Example 1(b) | Comparative Example 2(a) | Comparative Example 2(b) |
|---|---|---|---|---|---|
| Hydrogenation Pre-Treatment | Hydrocarbon Oil | Heavy FT Synthetic Oil | | Heavy FT Synthetic Oil | |
|  | Pre-Treatment | Hydrocracking | | None | |
|  | Catalyst | Hydrocracking Catalyst A-1 | | — | |
|  | Temperature, °C. | 318 | | — | |
|  | Hydrogen Partial Pressure, MPa | 4 | | — | |
|  | LHSV, h$^{-1}$ | 2 | | — | |
|  | Hydrogen/Oil Ratio, scf/bbl | 4000 | | — | |
|  | Cracking Ratio, % | 70 | | — | |
| Oil to be Treated Characteristics | T10, °C. | 345 | | 345 | |
|  | T50, °C. | 398 | | 399 | |
|  | T90, °C. | 453 | | 454 | |
|  | Acyclic Saturated Component, % | 100 | | 100 | |
|  | Isomer Ratio, % | 90 | | 10 | |
|  | Average Carbon Number | 28 | | 28 | |
|  | Index Value (1) | 0.15 | | 0.003 | |
|  | Index Value (2) | 0.15 | | 0.7 | |

TABLE 2-continued

| | | | | | |
|---|---|---|---|---|---|
| | Index Value (3) | 0.25 | | 0.02 | |
| | Index Value (4) | 28 | | 28 | |
| | Index Value (5) | 4.2 | | 19.6 | |
| Isomerization Dewaxing | Catalyst | Isomerization Dewaxing Catalyst C | Isomerization Dewaxing Catalyst C | Isomerization Dewaxing Catalyst C | Isomerization Dewaxing Catalyst C |
| | Temperature, ° C. | 320 | 310 | 320 | 340 |
| | Hydrogen Partial Pressure, MPa | 5 | 5 | 5 | 5 |
| | LHSV, h$^{-1}$ | 1 | 1 | 1 | 1 |
| | Hydrogen/Oil Ratio, scf/bbl | 3000 | 3000 | 3000 | 3000 |
| Hydrorefining | Catalyst | Hydrorefining Catalyst D | Hydrorefining Catalyst D | Hydrorefining Catalyst D | Hydrorefining Catalyst D |
| | Temperature, ° C. | 190 | 190 | 190 | 190 |
| | Hydrogen Partial Pressure, MPa | 5 | 5 | 5 | 5 |
| | LHSV, h$^{-1}$ | 1.5 | 1.5 | 1.5 | 1.5 |
| | Hydrogen/Oil Ratio, scf/bbl | 3000 | 3000 | 3000 | 3000 |
| | Base Oil Yield, % (Oil to be Treated) | 50 | 55 | 60 | 40 |
| Lubricant Base Oil 1 (70Pale Characteristics) | 100° C. Kinematic Viscosity, mm$^2$/s | 2.7 | 2.7 | 2.7 | 2.7 |
| | Pour Point, ° C. | −40 | −40 | −35 | −35 |
| | Viscosity Index | 120 | 123 | 133 | 130 |
| Lubricant Base Oil 2 (SAE-10 Characteristics) | 100° C. Kinematic Viscosity, mm$^2$/s | 3.9 | 3.9 | 3.9 | 3.9 |
| | Pour Point, ° C. | −35 | −25 | −10 | −25 |
| | Viscosity Index | 130 | 135 | 145 | 140 |
| Lubricant Base Oil 3 (SAE-20 Characteristics) | 100° C. Kinematic Viscosity, mm$^2$/s | — | — | — | — |
| | Pour Point, ° C. | — | — | — | — |
| | Viscosity Index | — | — | — | — |

| | | Comparative Example 3(a) | Comparative Example 3(b) | Comparative Example 4(a) | Comparative Example 4(b) |
|---|---|---|---|---|---|
| Hydrogenation Pre-Treatment | Hydrocarbon Oil Pre-Treatment | Heavy FT Synthetic Oil Hydrocracking | | Heavy Slack Wax Hydrocracking | |
| | Catalyst | Hydrocracking Catalyst A-1 | | Hydrocracking Catalyst A-2 | |
| | Temperature, ° C. | 319 | | 395 | |
| | Hydrogen Partial Pressure, MPa | 4 | | 5.8 | |
| | LHSV, h$^{-1}$ | 2 | | 1 | |
| | Hydrogen/Oil Ratio, scf/bbl | 4000 | | 3000 | |
| | Cracking Ratio, % | 70 | | 60 | |
| Oil to be Treated Characteristics | T10, ° C. | 463 | | 349 | |
| | T50, ° C. | 504 | | 402 | |
| | T90, ° C. | 526 | | 459 | |
| | Acyclic Saturated Component, % | 100 | | 80 | |
| | Isomer Ratio, % | 91 | | 90 | |
| | Average Carbon Number | 33 | | 28 | |
| | Index Value (1) | 0.16 | | 0.13 | |
| | Index Value (2) | 0.14 | | 0.13 | |
| | Index Value (3) | 0.26 | | 0.22 | |
| | Index Value (4) | 33 | | 28 | |
| | Index Value (5) | 4.6 | | 3.6 | |
| Isomerization Dewaxing | Catalyst | Isomerization Dewaxing Catalyst C | Isomerization Dewaxing Catalyst C | Isomerization Dewaxing Catalyst C | Isomerization Dewaxing Catalyst C |
| | Temperature, ° C. | 322 | 311 | 320 | 310 |
| | Hydrogen Partial Pressure, MPa | 5 | 5 | 5 | 5 |
| | LHSV, h$^{-1}$ | 1 | 1 | 1 | 1 |
| | Hydrogen/Oil Ratio, scf/bbl | 3000 | 3000 | 3000 | 3000 |
| Hydrorefining | Catalyst | Hydrorefining Catalyst D | Hydrorefining Catalyst D | Hydrorefining Catalyst D | Hydrorefining Catalyst D |
| | Temperature, ° C. | 190 | 190 | 225 | 225 |
| | Hydrogen Partial Pressure, MPa | 5 | 5 | 5 | 5 |
| | LHSV, h$^{-1}$ | 1.5 | 1.5 | 1.5 | 1.5 |
| | Hydrogen/Oil Ratio, scf/bbl | 3000 | 3000 | 3000 | 3000 |
| | Base Oil Yield, % (Oil to be Treated) | 51 | 56 | 50 | 55 |

TABLE 2-continued

| | | | | | |
|---|---|---|---|---|---|
| Lubricant Base Oil 1 (70Pale Characteristics) | 100° C. Kinematic Viscosity, mm²/s | — | — | 2.7 | 2.7 |
| | Pour Point, ° C. | — | — | −45 | −30 |
| | Viscosity Index | — | — | 110 | 115 |
| Lubricant Base Oil 2 (SAE-10 Characteristics) | 100° C. Kinematic Viscosity, mm²/s | — | — | 3.9 | 3.9 |
| | Pour Point, ° C. | — | — | −35 | −25 |
| | Viscosity Index | — | — | 123 | 125 |
| Lubricant Base Oil 3 (SAE-20 Characteristics) | 100° C. Kinematic Viscosity, mm²/s | 6.1 | 6.2 | — | — |
| | Pour Point, ° C. | −20 | −15 | — | — |
| | Viscosity Index | 150 | 153 | — | — |

According to a comparison between Examples and Comparative Examples, by selecting the oil to be treated having the index value (1) of 0.01 to 0.1, the index value (2) of 0.2 to 0.6, and the index value (3) of 0.05 to 0.2 and performing isomerization dewaxing at 280 to 360° C., a lubricating base oil having a high viscosity index and superior cold flow property can be obtained at a high yield.

100 . . . Lubricating Base Oil Production Apparatus, 10 . . . Pre-Treatment Reactor, 20 . . . Raw Material Atmospheric Distillation Tower, 21 . . . Raw Material Vacuum Distillation Tower, 30 . . . Isomerization dewaxing Reactor, 40 . . . Hydrorefining Reactor, 50 . . . Product Atmospheric Distillation Tower, 51 . . . Product Vacuum Distillation Tower.

The invention claimed is:

1. A method for producing a lubricating base oil, the method comprising:
  a first step of performing a $^{13}$C-NMR analysis with respect to an oil to be treated containing a normal paraffin and an isoparaffin, and selecting the oil to be treated based on the following index values (1), (2) and (3) in an obtained $^{13}$C-NMR spectrum,
  index value (1): a value obtained by dividing an integrated value of a peak assigned to a tertiary carbon atom by an integrated value of all peaks at 0 to 50 ppm,
  index value (2): a value obtained by dividing an integrated value of a peak assigned to a carbon atom constituting a hydrocarbon main chain by the integrated value of all peaks at 0 to 50 ppm, and
  index value (3): a value obtained by dividing an integrated value of a peak assigned to a branched CH$_3$ bonded to a fifth carbon atom or a carbon atom on an inner side thereof from a terminal carbon atom in the hydrocarbon main chain by an integrated value of all peaks at 10 to 25 ppm; and
  a second step of obtaining a dewaxed oil by isomerization dewaxing of the oil to be treated selected in the first step, wherein
  the first step is a step of selecting the oil to be treated having the index value (1) of 0.01 to 0.1, the index value (2) of 0.2 to 0.6, and the index value (3) of 0.05 to 0.2, and
  the second step is a step of performing isomerization dewaxing of the oil to be treated selected in the first step at a reaction temperature of 280 to 360° C.

2. The method according to claim 1, wherein
the first step is a step of selecting the oil to be treated having the index value (1) of 0.01 to 0.08, the index value (2) of 0.25 to 0.55, and the index value (3) of 0.05 to 0.18.

3. The method according to claim 1, wherein
the second step is a step of performing isomerization dewaxing of the oil to be treated selected in the first step at a reaction temperature of 300 to 340° C.

4. The method according to claim 1, wherein
the oil to be treated is selected based on additional index values (4) and (5):
index value (4): an average carbon number determined from a gas chromatography analysis of the oil to be treated, and
index value (5): a product of the index value (2) and the index value (4) of the oil to be treated,
wherein the oil to be treated selected in the first step has the index value (4) of from 23 to less than 29, and the index value (5) of from 5 to 19.

5. The method according to claim 1, wherein
the oil to be treated is selected based on additional index values (4) and (5):
index value (4): an average carbon number determined from a gas chromatography analysis of the oil to be treated, and
index value (5): a product of the index value (2) and the index value (4) of the oil to be treated,
wherein the oil to be treated selected in the first step has the index value (4) of from 31 to less than 35, and the index value (5) of from 8 to 25.

* * * * *